US009895386B2

(12) United States Patent
Charan et al.

(10) Patent No.: US 9,895,386 B2
(45) Date of Patent: *Feb. 20, 2018

(54) ANTIBIOTIC FORMULATIONS, UNIT DOSES, KITS, AND METHODS

(71) Applicant: Bayer Intellectual Property GMBH, Monheim am Rhein (DE)

(72) Inventors: Chatan Charan, San Jose, CA (US); Sarvajna Dwivedi, Redwood City, CA (US)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/143,009

(22) Filed: Apr. 29, 2016

(65) Prior Publication Data
US 2016/0317562 A1 Nov. 3, 2016

Related U.S. Application Data

(60) Continuation of application No. 13/471,126, filed on May 14, 2012, now Pat. No. 9,351,929, which is a division of application No. 12/341,780, filed on Dec. 22, 2008, now abandoned, which is a continuation of application No. 11/529,128, filed on Sep. 28, 2006, now abandoned.

(60) Provisional application No. 60/722,564, filed on Sep. 29, 2005.

(51) Int. Cl.
| *A61K 9/00* | (2006.01) |
| *A61K 9/12* | (2006.01) |
| *A61K 31/7036* | (2006.01) |
| *A61K 31/573* | (2006.01) |
| *A61K 9/08* | (2006.01) |
| *A61M 16/14* | (2006.01) |
| *A61K 9/19* | (2006.01) |
| *A61K 31/7034* | (2006.01) |
| *A61M 11/00* | (2006.01) |
| *A61J 1/06* | (2006.01) |
| *A61J 1/14* | (2006.01) |
| *A61M 16/04* | (2006.01) |

(52) U.S. Cl.
CPC .......... *A61K 31/7036* (2013.01); *A61J 1/065* (2013.01); *A61J 1/1412* (2013.01); *A61K 9/0019* (2013.01); *A61K 9/0078* (2013.01); *A61K 9/08* (2013.01); *A61K 31/573* (2013.01); *A61K 31/7034* (2013.01); *A61M 11/001* (2014.02); *A61M 16/04* (2013.01); *A61K 9/19* (2013.01); *A61M 2202/064* (2013.01)

(58) Field of Classification Search
CPC ...... A61K 9/08; A61K 9/0078; A61K 9/0019; A61K 9/19; A61K 31/573; A61K 31/7034; A61K 31/7036; A61M 11/001; A61M 16/04
See application file for complete search history.

(56) References Cited

U.S. PATENT DOCUMENTS

| 4,146,971 A | 4/1979 | Bornstein et al. |
| 4,684,643 A | 8/1987 | Buddenbaum et al. |
| 5,118,494 A | 6/1992 | Schultz et al. |
| 5,225,183 A | 7/1993 | Purewal et al. |
| 5,290,540 A | 3/1994 | Prince et al. |
| 5,373,095 A | 12/1994 | Johnson et al. |
| 5,409,704 A | 4/1995 | Bally et al. |
| 5,474,759 A | 12/1995 | Fassberg et al. |
| 5,492,688 A | 2/1996 | Byron et al. |
| 5,508,023 A | 4/1996 | Byron et al. |
| 5,508,269 A | 4/1996 | Smith et al. |
| 5,605,674 A | 2/1997 | Purewal et al. |
| 5,621,085 A | 4/1997 | Dall'Asta et al. |
| 5,655,520 A | 8/1997 | Howe et al. |
| 5,656,735 A | 8/1997 | Dall'Asta et al. |
| 5,663,152 A | 9/1997 | Hayano et al. |
| 5,681,545 A | 10/1997 | Purewal et al. |
| 5,683,677 A | 11/1997 | Purewal et al. |
| 5,707,352 A | 1/1998 | Sekins et al. |
| 5,716,931 A | 2/1998 | Molina y Vedia et al. |
| 5,756,120 A | 5/1998 | Hersch et al. |
| 5,763,587 A | 6/1998 | Mangia |
| 5,840,277 A | 11/1998 | Ghio et al. |

(Continued)

FOREIGN PATENT DOCUMENTS

| WO | WO-91/04011 A1 | 4/1991 |
| WO | WO-91/11173 A1 | 8/1991 |
| WO | WO-92/00107 A1 | 1/1992 |
| WO | WO-95/17195 A1 | 6/1995 |
| WO | WO-01/02024 A1 | 1/2001 |

(Continued)

OTHER PUBLICATIONS

Bedford Laboratories product insert, Amikacin Sulfate Injection, USP (1998).
De Young et al., "The Aerodose Multidose Inhaler Device Design and Delivery Characteristics", Respiratory Drug Delivery VI, pp. 91-95 (1998).

(Continued)

*Primary Examiner* — Mina Haghighatian
(74) *Attorney, Agent, or Firm* — White & Case LLP

(57) ABSTRACT

An aqueous or powder composition includes anti-gram-negative antibiotic or salt thereof being present at an amount ranging from about 100 mg/ml to about 200 mg/ml. Another aqueous or powder composition includes anti-gram-positive antibiotic or salt thereof being present at a concentration ranging from about 0.6 to about 0.9 of the water solubility limit, at 25° C. and 1.0 atmosphere, of the anti-gram-positive antibiotic or salt thereof. Other embodiments include unit doses, kits, and methods.

10 Claims, 11 Drawing Sheets

(56) References Cited

U.S. PATENT DOCUMENTS

| | | | |
|---|---|---|---|
| 5,922,675 | A | 7/1999 | Baker et al. |
| 6,083,922 | A | 7/2000 | Montgomery |
| 6,265,386 | B1 | 7/2001 | Campbell |
| 6,309,623 | B1 | 10/2001 | Weers et al. |
| 6,316,433 | B1 | 11/2001 | Rose et al. |
| 6,387,886 | B1 | 5/2002 | Montgomery et al. |
| 6,410,533 | B1 | 6/2002 | Hirth et al. |
| 6,475,992 | B2 | 11/2002 | McLean |
| 6,565,873 | B1 | 5/2003 | Shefer et al. |
| 6,566,354 | B1 | 5/2003 | Rose et al. |
| 6,572,849 | B2 | 6/2003 | Shahinian, Jr. |
| 6,576,224 | B1 | 6/2003 | Osbakken et al. |
| 6,596,261 | B1 | 7/2003 | Adjei et al. |
| 6,858,589 | B2 | 2/2005 | McLean |
| 6,890,907 | B2 | 5/2005 | Speirs et al. |
| 6,968,840 | B2 | 11/2005 | Smith et al. |
| 6,987,094 | B2 | 1/2006 | Malvolti et al. |
| 7,201,167 | B2 | 4/2007 | Fink et al. |
| 7,220,727 | B2 | 5/2007 | Haddad et al. |
| 7,290,541 | B2 | 11/2007 | Lvri et al. |
| 7,331,339 | B2 | 2/2008 | Smith et al. |
| 7,368,102 | B2 | 5/2008 | Tarara et al. |
| 7,696,178 | B2 | 4/2010 | Malvolti et al. |
| 7,758,886 | B2 | 7/2010 | Jauernig et al. |
| 7,971,588 | B2 | 7/2011 | Fink et al. |
| 8,196,573 | B2 | 6/2012 | Fink et al. |
| 8,336,545 | B2 | 12/2012 | Fink et al. |
| 9,205,050 | B2 | 12/2015 | Charan et al. |
| 9,351,929 | B2 * | 5/2016 | Charan ................. A61K 9/0078 |
| 9,351,930 | B2 * | 5/2016 | Charan ................. A61K 9/0078 |
| 2002/0134373 | A1 * | 9/2002 | Gonda ............... A61M 15/0028 128/200.14 |
| 2003/0129140 | A1 | 7/2003 | Tarara et al. |
| 2003/0176327 | A1 | 9/2003 | Cassell et al. |
| 2004/0011358 | A1 | 1/2004 | Smaldone et al. |
| 2004/0035413 | A1 | 2/2004 | Smaldone et al. |
| 2004/0035490 | A1 | 2/2004 | Power |
| 2004/0131555 | A1 | 7/2004 | Speirs et al. |
| 2004/0265241 | A1 | 12/2004 | Speirs et al. |
| 2005/0009731 | A1 * | 1/2005 | Desai .................... A61J 1/1412 435/6.13 |
| 2005/0139211 | A1 | 6/2005 | Alston et al. |
| 2005/0163722 | A1 | 7/2005 | Malvolti et al. |
| 2005/0171035 | A1 | 8/2005 | Haddad et al. |
| 2005/0207987 | A1 | 9/2005 | Speirs et al. |
| 2005/0211245 | A1 | 9/2005 | Smaldone et al. |
| 2005/0211253 | A1 | 9/2005 | Smaldone et al. |
| 2005/0217666 | A1 | 10/2005 | Fink et al. |
| 2005/0235987 | A1 | 10/2005 | Smaldone et al. |
| 2005/0244339 | A1 | 11/2005 | Jauernig et al. |
| 2006/0263570 | A1 | 11/2006 | Bunyan |
| 2007/0071686 | A1 | 3/2007 | Lintz et al. |
| 2007/0116649 | A1 | 5/2007 | Charan et al. |
| 2007/0267010 | A1 | 11/2007 | Fink et al. |
| 2009/0288658 | A1 | 11/2009 | Charan et al. |
| 2010/0286031 | A1 | 11/2010 | Charan et al. |
| 2013/0014759 | A1 | 1/2013 | Montgomery |

FOREIGN PATENT DOCUMENTS

| | | |
|---|---|---|
| WO | WO-2001/4752 | 5/2001 |
| WO | WO-03/004005 A1 | 1/2003 |
| WO | WO-03/026669 A1 | 4/2003 |
| WO | WO-03/053411 A1 | 7/2003 |
| WO | WO-2004/052333 A1 | 6/2004 |
| WO | WO-2004/071368 A2 | 8/2004 |
| WO | WO-2004/110346 A2 | 12/2004 |
| WO | WO-2005/037256 A2 | 4/2005 |
| WO | WO-2006/002896 A1 | 1/2006 |
| WO | WO-2006/055950 A1 | 5/2006 |
| WO | WO-2006/102345 A2 | 9/2006 |
| WO | WO-2007/124382 A2 | 11/2007 |
| WO | WO-2009/042187 A1 | 4/2009 |
| WO | WO-2009/120619 A2 | 10/2009 |

OTHER PUBLICATIONS

Dequin et al., "Characterization on the Bench of an Amikacin Aerosol Before Clinical Studies", Journal of Aerosol Medicine, vol. 10, No. 3, 1997 pp. 221-230.

Faurisson et al., "A Simple Tool for Monitoring Nebulized Amikacin Treatments Based on a Single Urine Assay", 14(1): 73-81 (2001).

Faurisson, F., et al., "Pharmacokinetics of Aerosolized Amikacin in Cystic Fibrosis", Am. Rev. Respir. Dis., 143:A294 (Abstract) (1991).

Fink, J. B., et al., "Nebulizer Efficiency Measured In Vitro Agrees With Sputum Concentration of Amikacin in Patients on Mechanical Ventilation", Respiratory Drug Delivery Conference (RDD) (Apr. 2004).

Goldstein et al., "Lung Tissue Concentrations of Nebulized Amikacin during Mechanical Ventilation in Piglets with Healthy Lungs", Am J Respir Critical Care Med, vol. 165, pp. 171-175 (2002).

Gooch, "Stability of Albuterol and tobramycin when mixed for aerosol administration," Elsevier Science Pub., Database Embase (online), Database accession No. EMB-1992054364 abstract (1991).

Gooch, "Stability of Albuterol and Tobramycin When Mixed for Aerosol Administration," Respiratory Care, 36(12):1387-1390, XP002445579 (Dec. 1991).

Le Brun et al., "Can Tobramycin Inhalation be Improved with a Jet Nebulizer?", Therapeutic Drug Monitoring, 21:618-21 (1999).

Le Brun et al., "Inhalation of tobramycin in cystic fibrosis Part 2: Optimization of the tobramycin solution for a jet and an ultrasonic nebulizer", International Journal of Pharmaceutics 189 (1999) 215-225.

McPeck et al., "Aerosol Delivery During Continuous Nebulization", CHEST, vol. 111(5), pp. 1200-1205 (1997).

Mercier, E., et al., "Aerosol Delivery of Amikacin by Three Nebulizers of Varying Efficiency in Patients on Mechanical Ventilators", American Thoracic Society International Conference (ATS), poster (May 2004).

Palmer et al., "Aerosolized antibiotics in mechanically ventilated patients: Delivery and response", Critical Care Medicine, vol. 26(1), Jan. 1998, pp. 31-39.

Physicians' Desk Reference, Amikacin Sulfate Injection, USP (1999).

Santre et al., "Amikacin Levels in Bronchial Secretions of 10 Pneumonia Patients with Respiratory Support Treated Once Daily versus Twice Daily", Antimicrbial Agents and Chemotherapy, Jan. 1995, p. 264-267.

Sicor product insert, Amikacin Sulfate Injection, USP (1995).

Webb and Dodd, "Nebulised antibiotics for adults with cystic fibrosis", Thorax 1997;52(SuppJ 2):S69-S71.

Weber et al., "Effect of Nebulizer Type and Antibiotic Concentration on Development Performance", Pediatric Pulmonology, 23: 249-260 (1997).

Donald P. Levine, Vancomycin: A History. CID 2006. vol. 42, Suppl 1, pp. S5-S12.

Generali et al. Vancomycin: Aerolization. Hospital Pharmacy, Jul. 2004. vol. 39 No. 7, pp. 638-647.

Maiz et al. Aerosolized vancomycin for the treatment of methicillin-resistant *Staphylococcus aureous* infection in cystic fibrosis. Pediatr Pulmonol. 1998, vol. 26, No. 4, pp. 287-288.

Vancomycin Hydrochloride (vancomycin hydrochloride) Injection, Powder, Lyophilized, for Solution, [HOSPIRA, INC], date: Jul. 2004, accessed online at http://dailymed.nlm.nih.gov/dailymed/archives/fdaDrugInfo.cfm?archiveid=2536, 14 pages.

* cited by examiner

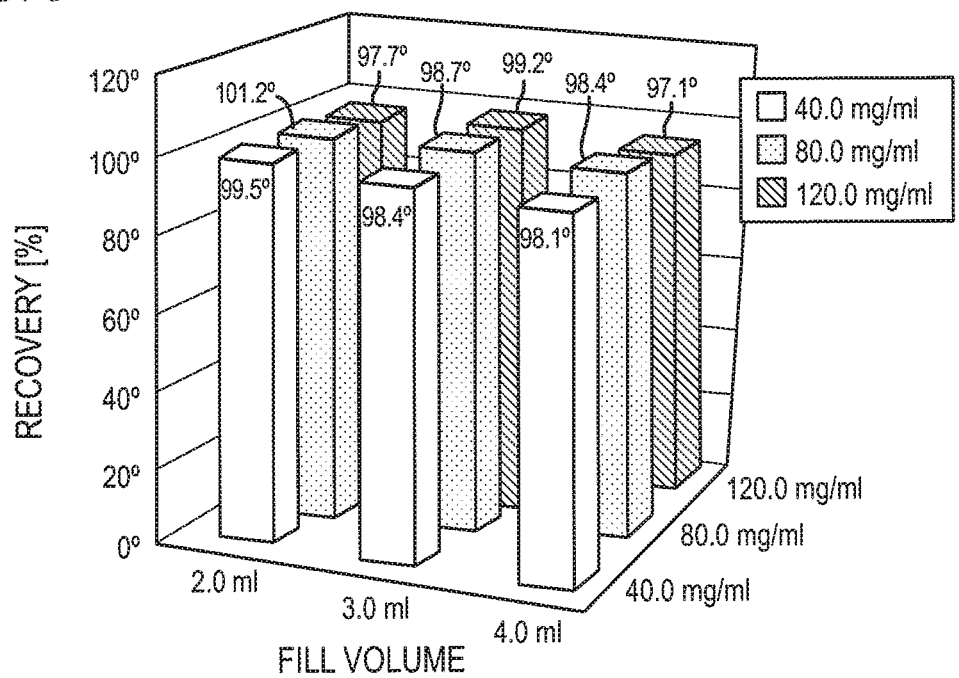
FIG. 3 TOTAL DOSE RECOVERED
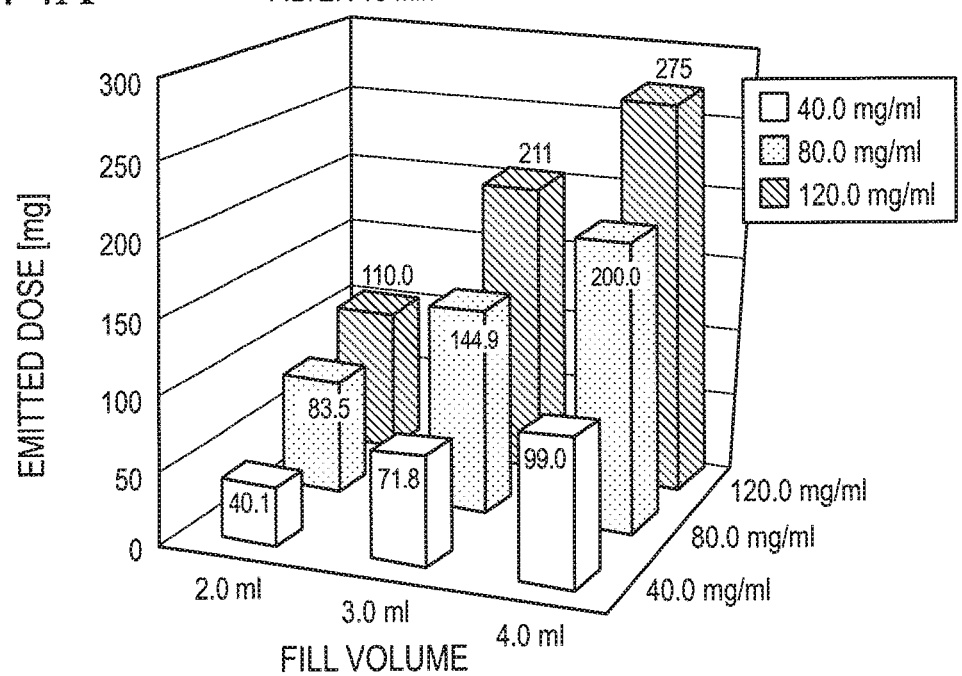
FIG. 4A FILTER 15 min

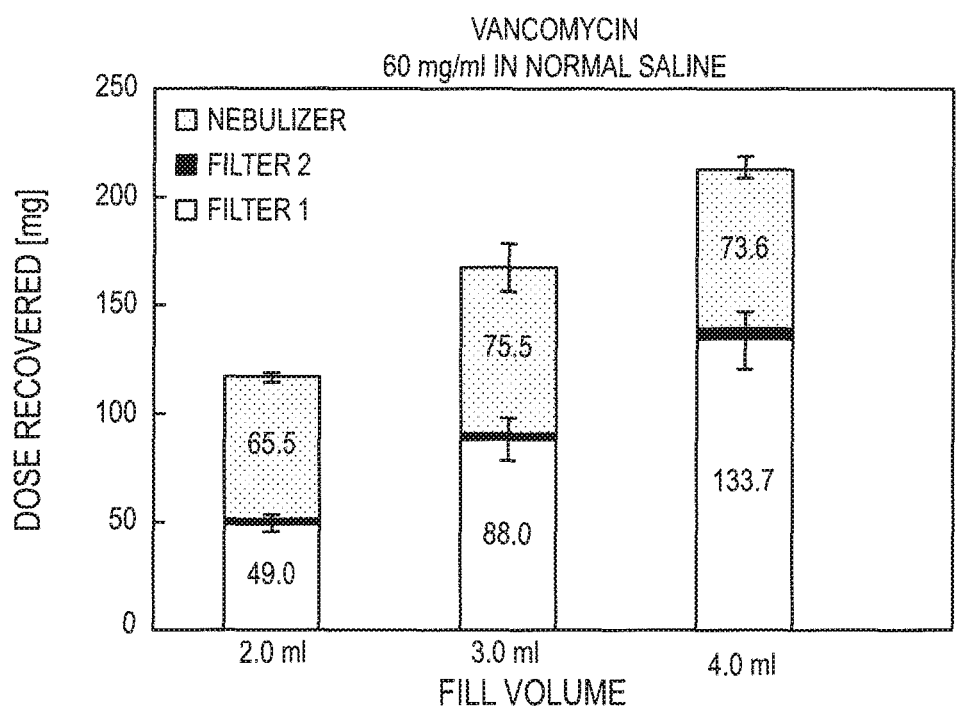
FIG. 6
FIG. 7
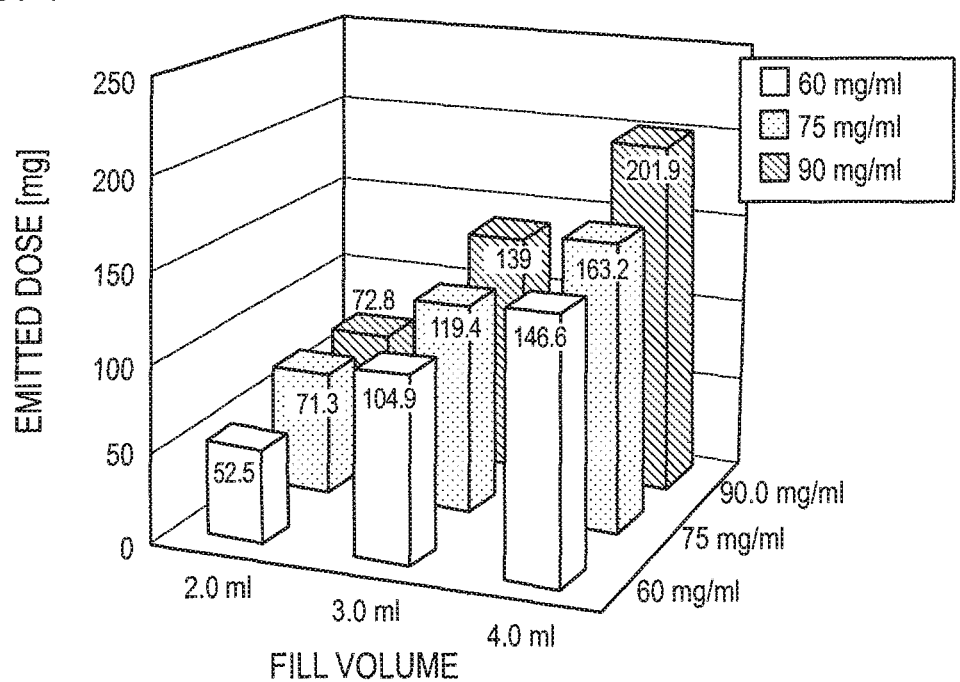

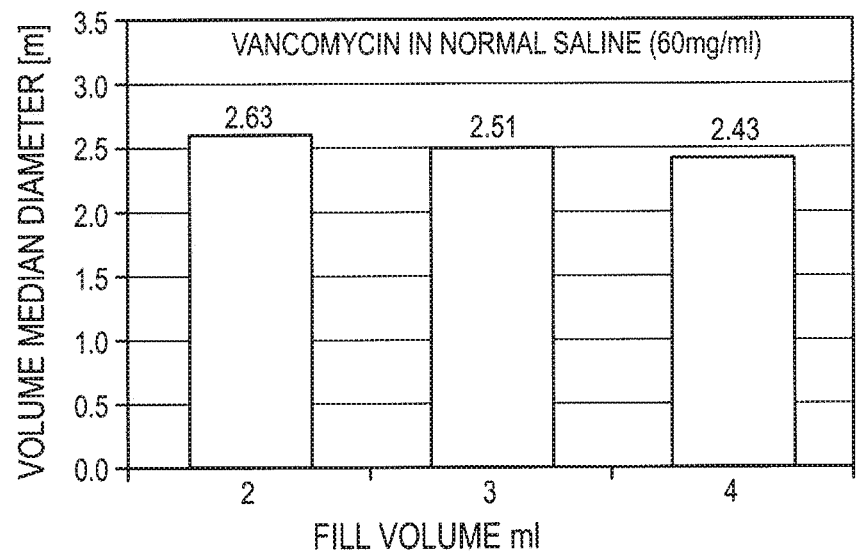
FIG. 13
FIG. 14
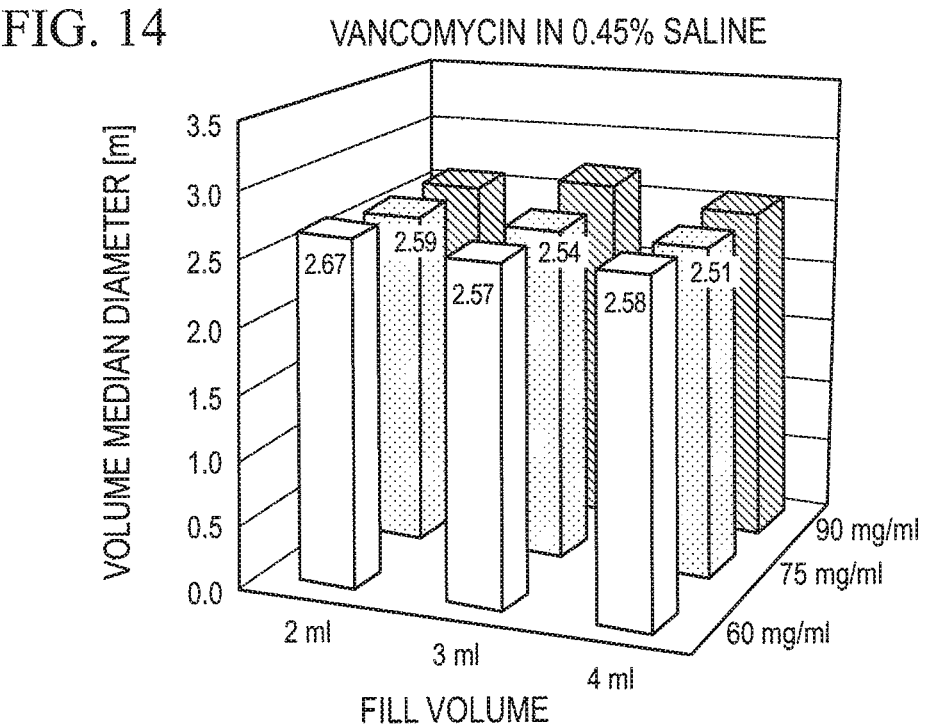

FIG. 15
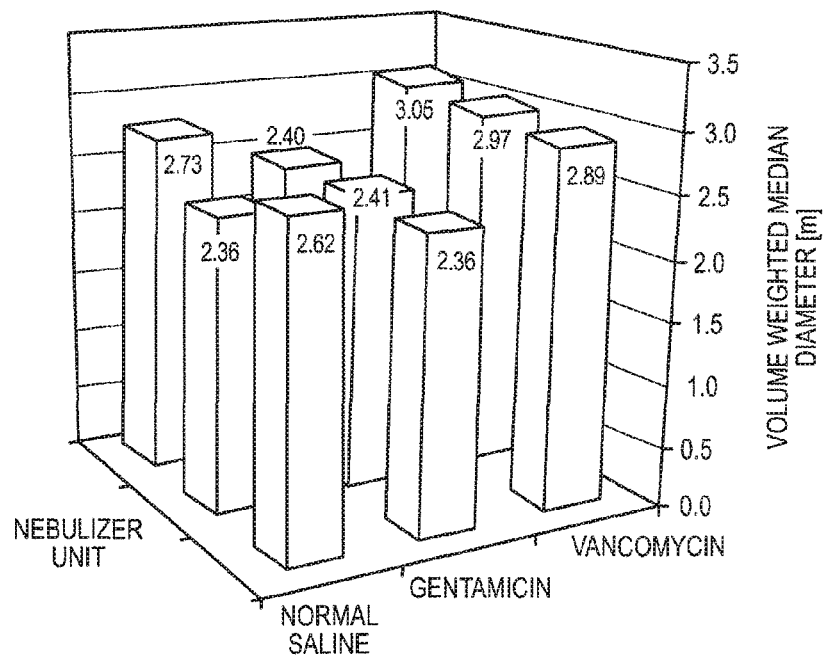
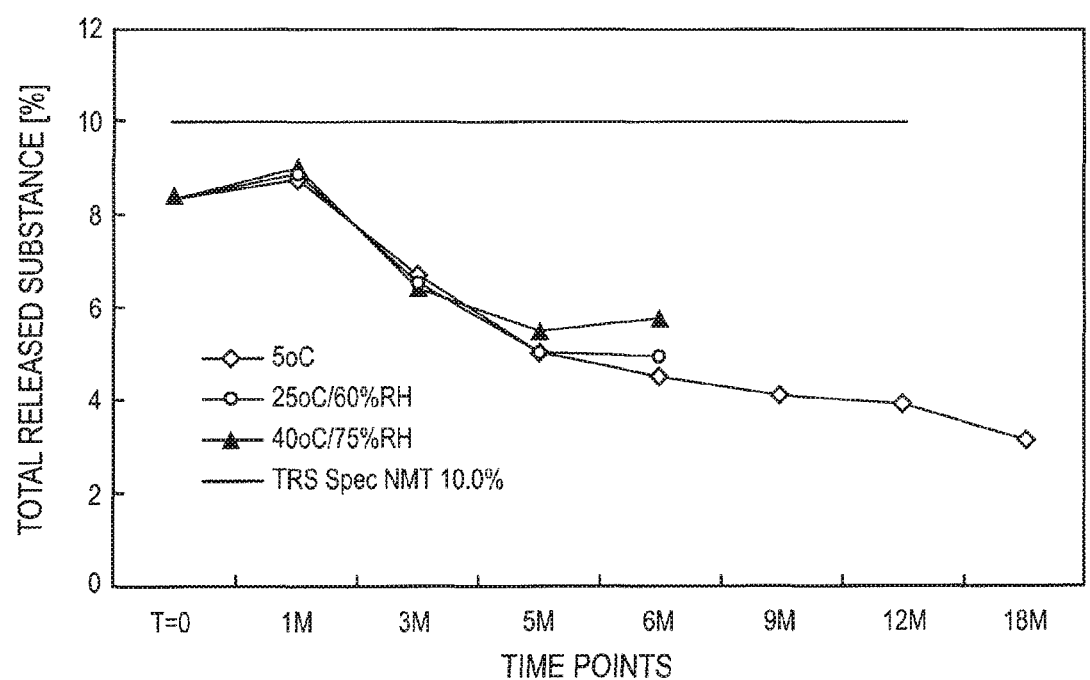
FIG. 16

ANTIBIOTIC FORMULATIONS, UNIT DOSES, KITS, AND METHODS

CROSS-REFERENCE TO RELATED APPLICATIONS

This application is a continuation of U.S. application Ser. No. 13/471,126, which is a divisional application of U.S. application Ser. No. 12/341,780, filed Dec. 22, 2008, which is a continuation of U.S. application Ser. No. 11/529,128, filed Sep. 28, 2006, which claims priority to U.S. Provisional Application No. 60/722,564, filed Sep. 29, 2005. The foregoing applications are incorporated herein by reference in their entirety.

Field of the Invention

The present invention relates to anti-infective, such as antibiotic formulations, unit doses, kits, and methods, and in particular to aminoglycoside formulations, unit doses, kits, and methods Background of the Invention The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before the body can effectively absorb them. Inhaleable drug delivery, where a patient orally or nasally inhales an aerosolized pharmaceutical formulation to deliver the formulation to the patient's respiratory tract, may also be effective and/or desirable. In one inhalation technique, an aerosolized pharmaceutical formulation provides local therapeutic treatment and/or prophylaxis to a portion of the respiratory tract, such as the lungs, to treat respiratory diseases such as asthma and emphysema and/or to treat local lung infections, such as fungal infections and cystic fibrosis. In another inhalation technique, a pharmaceutical formulation is delivered deep within a patient's lungs where it may be absorbed into the bloodstream for systemic delivery of the formulation throughout the body. Many types of aerosol bat ion devices exist including devices comprising a pharmaceutical formulation stored in or with a propellant, devices that aerosolize a powder, devices which use a compressed gas or other mechanism to aerosolize a liquid pharmaceutical formulation, and similar devices.

One known aerosolization device is commonly referred to as a nebulizer. A nebulizer imparts energy into a liquid pharmaceutical formulation to aerosolize the liquid, and to allow delivery to the pulmonary system, e.g. the lungs, of a patient. A nebulizer comprises a liquid delivery system, such as a container having a reservoir that contains a liquid pharmaceutical formulation. The liquid pharmaceutical formulation generally comprises an active agent that is either in solution or suspended within a liquid medium. In one type of nebulizer, generally referred to as a jet nebulizer, compressed gas is forced through an orifice in the container. The compressed gas forces liquid to be withdrawn through a nozzle, and the withdrawn liquid mixes with the flowing gas to form aerosol droplets. A cloud of droplets is then administered to the patient's respiratory tract. In another type of nebulizer, generally referred to as a vibrating mesh nebulizer, energy, such as mechanical energy, vibrates a mesh. This vibration of the mesh aerosolizes the liquid pharmaceutical formulation to create an aerosol cloud that is administered to the patient's lungs. In still another type of nebulizer, ultrasonic waves are generated to directly vibrate and aerosolize the pharmaceutical formulation.

Nebulizers are often used to deliver (1) an aerosolized pharmaceutical formulation to a hospitalized or non-ambulatory patient; (2) large doses of aerosolized active agent; and/or (3) an aerosolized pharmaceutical formulation to a child or other patient unable to receive a dry powder or propellant based pharmaceutical formulation.

Nebulizers are useful for delivering an aerosolized pharmaceutical formulation to the respiratory tract of a patient who is breathing under the assistance of a ventilator. But there are problems associated with the introduction of aerosolized pharmaceutical formulation into ventilator circuits. For example, by introducing the aerosolized pharmaceutical formulation into the inspiratory line of the ventilator, significant residence volume exists between the point of introduction and the patient's lungs. Accordingly, large amounts of aerosolized pharmaceutical formulation are needed and much of the formulation is lost to the exhalation line. This problem is exacerbated when the nebulizer is used in conjunction with ventilators having continual bias flows. In addition, the large residence volume in the ventilator line may dilute the aerosolized pharmaceutical formulation to an extent where the amount delivered to the patient is difficult to reproduce consistently.

U.S. Published Application Nos. 2004/0011358, 2004/0035490, and 2004/0035413, which are incorporated herein by reference in their entireties, disclose methods, devices, and formulations for targeted endobronchial therapy. Aerosolized antibiotics are delivered into a ventilator circuit. The aerosol generator, e.g., nebulizer, may be placed in the lower part of a Y-piece, for example, distal to the Y, to the proximal to a patient airway and/or endrotracheal tube.

U.S. Pat. Nos. 5,508,269 and 6,890,907, which are incorporated herein by reference in their entireties, disclose aminoglycoside solutions for nebulization. The '269 patent discloses that if the solution approaches the solubility of tobramycin, 160 mg/ml, precipitation on storage is expected. The '269 patent also discloses that a higher concentration of tobramycin than is clinically needed is economically disadvantageous. Further the '269 patent discloses that a more concentrated solution will increase the osmolality of the solution, thus decreasing the output of the formulation with both jet and ultrasonic nebulizers. The '269 patent discloses that the alternative of a more concentrated solution in a smaller total volume is also disadvantageous. The '269 patent further discloses that most nebulizers have a dead space volume of 1 ml, i.e., that of the last 1 ml of solution is wasted because the nebulizer is not performing. Therefore, while for example, a 2 ml solution would have 50% wastage, the 5 ml solution (the capacity of the nebulizer) has only 20% wastage. Additionally, the '269 patent discloses that since there is no sufficient aerosolization of the drug into the small particles, the drug in large particles or as a solution is deposited in the upper airways and induces cough and may also cause bronchospasm. According to the '269 patent, large aerosol particles also limit the drug delivery.

There remains, however, a need for improved antibiotic formulations, such as antibiotic formulations for nebulization. There also remains a need for improved unit doses and kits of antibiotic formulations. Accordingly, there also remains a need for improved methods of making and/or using such antibiotic formulations.

SUMMARY OF THE INVENTION

Accordingly, one or more embodiments of the present invention satisfies one or more of these needs. Thus the present invention provides antibiotic formulations, such as antibiotic formulations for nebulization. The present invention also provides unit doses and kits of antibiotic formulations. The present invention, further provides methods of making and/or using such antibiotic formulations. Other features and advantages of the present invention will be set forth in the description of invention that follows, and will be apparent, in part, from the description or may be learned by practice of the invention. The invention will be realized and attained by the devices and methods particularly pointed out in the written description and claims hereof.

In one aspect, one or more embodiments are directed to an aqueous composition, comprising an antibiotic or salt thereof being present at a therapeutic-effective (including prophylatic-effective) amount. In one or more embodiments, the therapeutic-effective amount is based upon aerosolized administration to the pulmonary system.

In one aspect, one or more embodiments are directed to an aqueous composition, comprising anti-gram-negative antibiotic or salt thereof being present at an amount ranging from about 90 mg/ml to about 300 mg/ml.

In another aspect, an aqueous composition comprises anti-gram-negative antibiotic or salt thereof, and optionally, a bronchodilator.

In still another aspect, an aqueous composition comprises anti-gram-positive antibiotic or salt thereof being present at a concentration ranging from about 0.6 to about 0.9 of the water solubility limit, at 25° C. and 1.0 atmosphere, of the anti-gram-positive antibiotic or salt thereof.

In yet another aspect, a unit dose comprises a container and an aqueous composition, comprising anti-gram-negative antibiotic or salt thereof being present at a concentration ranging from about 100 mg/ml to about 200 mg/ml.

In still another aspect, a kit comprises a first container containing a first aqueous solution comprising an anti gram-negative antibiotic or salt thereof; and a second container containing a second aqueous solution comprising an anti gram-negative antibiotic or salt thereof. A concentration, or an amount, or both of the first aqueous solution is different from a concentration, or an amount, or both, of the second aqueous solution.

In yet another aspect, a kit comprises a first container containing a first, aqueous solution comprising anti gram-negative antibiotic or salt thereof, and a second container containing a second aqueous solution comprising anti gram-positive antibiotic or salt thereof.

In another aspect, a unit dose comprises a container and a powder comprising an antibiotic or salt thereof, wherein the powder is present in an amount ranging from about 550 mg to about 900 mg.

In still another aspect, a unit dose comprises a container; and a powder comprising an antibiotic or salt thereof, wherein the powder is present in an amount ranging from about 150 mg to about 450 mg.

In yet another aspect, a kit comprises a first container containing a first composition comprising anti-gram-positive or an anti gram-negative antibiotic or salt thereof and a second container containing a second composition comprising water. The first composition and/or the second composition comprises osmolality adjuster.

In another aspect, a kit comprises a first container containing a powder comprising anti-gram-positive antibiotic or salt thereof and a second container containing a powder comprising anti gram-positive antibiotic or salt thereof. A concentration, or an amount, or both, of the anti gram-positive antibiotic or salt thereof in the first container is different from a concentration, or an amount, or both, of the anti gram-positive antibiotic or salt thereof in the second container.

In a further aspect, a kit comprises a first container containing a solution comprising anti gram-negative antibiotic or salt thereof and a second container containing a powder comprising anti gram-positive antibiotic or salt thereof.

In still another aspect, a method of administering an antibiotic formulation to a patient in need thereof comprises aerosolizing an antibiotic formulation to administer the antibiotic formulation to the lungs of the patient. The antibiotic formulation has a concentration of antibiotic or salt thereof ranging from about 90 mg/ml to about 300 mg/ml.

In another aspect, a method of administering an antibiotic formulation to a patient in need thereof comprises inserting a tube into a trachea of a patient. The method also comprises aerosolizing an antibiotic formulation to administer the antibiotic formulation to the lungs of the patient. The antibiotic formulation consists essentially of anti-gram-negative antibiotic or salt thereof and water.

In yet another aspect, a method of administering an antibiotic formulation to a patient in need thereof comprises aerosolizing an antibiotic formulation to administer the antibiotic formulation to the lungs of the patient. The antibiotic formulation comprises an antibiotic or salt thereof at a concentration ranging from about 0.7 to about 0.9 of the water solubility limit, at 25° C. and 1.0 atmosphere, of the antibiotic or salt thereof.

In a further aspect, a method of administering an antibiotic formulation to a patient in need thereof comprises dissolving an antibiotic or salt thereof in a solvent to form an antibiotic formulation, wherein the antibiotic or salt thereof is present at a concentration ranging from about 0.6 to about 0.9 of the water solubility limit, at 25° C. and 1.0 atmosphere, of the antibiotic or salt thereof. The method also includes aerosolizing the antibiotic formulation to administer the antibiotic formulation to the lungs of the patient.

In yet another aspect, a method of administering an antibiotic formulation to a patient in need thereof comprises dissolving an antibiotic or salt thereof in a solvent to form an antibiotic formulation. The method also includes aerosolizing the antibiotic formulation to administer the antibiotic formulation to the lungs of the patient, wherein the aerosolizing is conducted within about 16 hours of the dissolving.

In another aspect, a method involves forming a powder comprising an antibiotic or salt thereof. The method includes dissolving an antibiotic or salt thereof in a solvent to form a solution having a concentration ranging from about 60 mg/ml to about 120 mg/ml. The method also includes lyophilizing the solution to form the powder.

In another aspect, a method involves forming a powder comprising an antibiotic or salt thereof. The method comprises dissolving an antibiotic or salt thereof in a solvent to form a solution having a volume ranging from about 4.5 ml to about 5.5 ml. The method also includes lyophilizing the solution to form the dry powder.

In another aspect, any method which comprises forming a powder may also include a method of reconstituting the powder to form a liquid. Similarly any method which comprises forming a liquid comprising an antibiotic (such as a solution) may also include a method of removing the liquid to yield a powder.

In another aspect, any two or more of any of the foregoing features, aspects versions or embodiments are combined.

BRIEF DESCRIPTION OF THE DRAWINGS

The present invention is further described in the description of invention that follows, in reference to the noted plurality of non-limiting drawings, wherein:

FIG. 2A shows an exemplary off-ventilator configuration of a pulmonary drug delivery system according to embodiments of the invention.

FIG. 2B is a schematic view of a pharmaceutical delivery device of one or more embodiments of the present invention, useful for delivery of aerosolized medicaments.

FIG. 3 shows total drug recovered (nebulizer+filters) for gentamicin as a function of fill mass and solution strength.

FIGS. 4a-b show emitted dose of gentamicin as a function of solution strength and fill volume, after nebulization (FIG. 4a) for 15 minutes, and (FIG. 4) 30 minutes.

FIG. 6 shows distribution of nebulized vancomycin (60 mg/ml solution in normal saline) as a function of fill volume.

FIG. 7 shows emitted dose as a function of solution strength and fill volume, for the case of vancomycin solution in 0.45% saline.

FIG. 13 shows volume median diameter for nebulized vancomycin (60 mg/ml solution in normal saline) as a function of nebulizer fill volume.

FIG. 14 shows volume median diameter for nebulized vancomycin (solution in 0.45% saline) as a function of solution strength and fill volume.

FIG. 15 shows volume median diameter for antibiotic drug and placebo solutions.

FIG. 16 is a graph showing amikacin stability over time (as % related substance) for a formulation according to one or more embodiments of the present invention, wherein the formulation was stored at three different storage conditions.

DESCRIPTION OF THE INVENTION

Figure 1A:
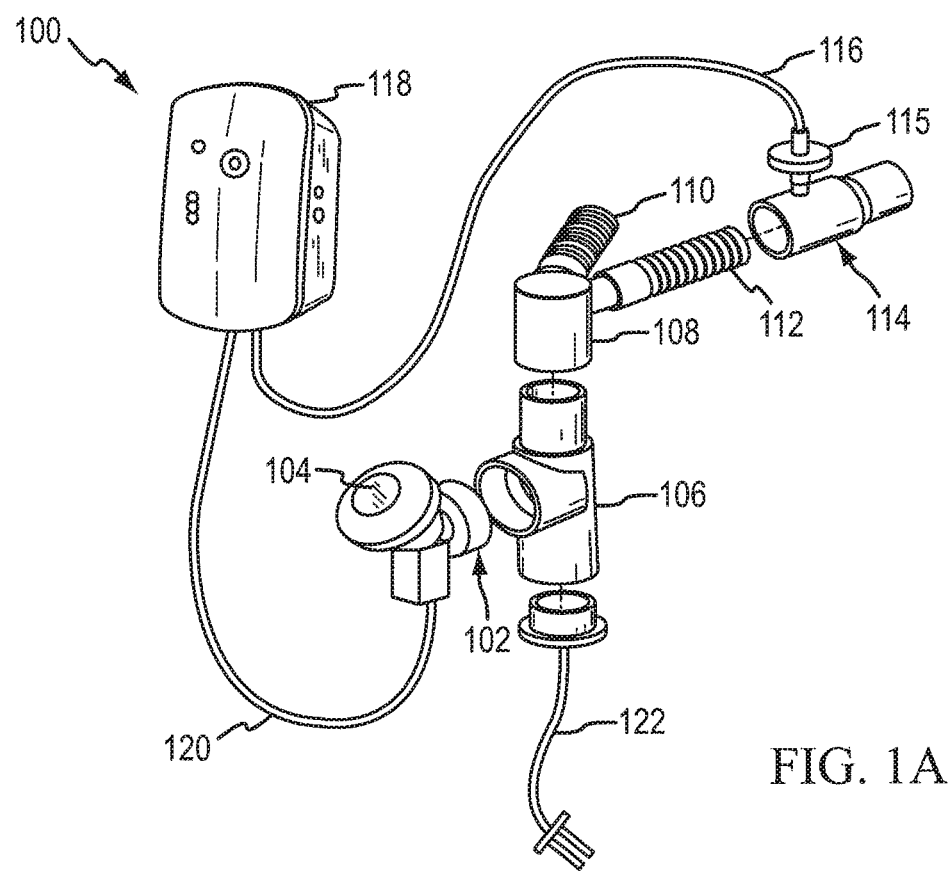
FIG. 1A illustrates components of a pulmonary drug delivery system according to embodiments of the present invention.

Unless otherwise stated, a reference to a compound or component includes the compound or component by itself, as well as in combination with other compounds or components, such as mixtures of compounds.

As used herein, the singular forms "a," "an," and "the" include the plural reference unless the context dearly dictates otherwise.

Reference herein to "one embodiment", "one version" or "one aspect" shall include one or more such embodiments, versions or aspects, unless otherwise clear from the context.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size.

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

Anti-gram negative, and gram-negative antibiotic are used interchangeably to refer to antibiotic active agents (and formulations comprising such active agents) which have effectiveness against gram negative bacteria. Similarly, anti-gram positive, and gram-positive antibiotic are used interchangeably to refer to antibiotic active agents (and formulations comprising such active agents) which have effectiveness against gram positive bacteria.

"Antibiotic" moreover includes anti-infectives, such as anti virals and antifungals, as well as antibiotics, unless the context indicates otherwise.

"Pharmaceutic formulation" and "composition" may be sometimes used interchangeably to refer to a formulation comprising an antibiotic.

As an overview, in one or more embodiments, an aqueous composition comprises anti-gram-negative and/or anti-gram positive antibiotic or salt thereof being present at an amount ranging from about 100 mg/ml to about 200 mg/ml.

In one or more embodiments, an aqueous composition comprises an antibiotic or salt thereof, and bronchodilator.

In one or more embodiments, an aqueous composition comprises an antibiotic or salt thereof being present at a concentration ranging from about 0.6 to about 0.9 of the water solubility limit, at 25° C. and 1.0 atmosphere, of the antibiotic or salt thereof.

In one or more embodiments, a unit dose comprises a container and an aqueous composition, comprising an anti-gram-negative antibiotic or salt thereof at a concentration ranging from about 100 mg/ml to about 200 mg/ml.

In one or more embodiments, a kit comprises a first container containing a first aqueous solution comprising anti-gram-negative antibiotic or salt thereof; and a second container containing a second aqueous solution comprising anti-gram-negative antibiotic or salt thereof. A concentration, or an amount, or both, of the first aqueous solution is different from a concentration, or an amount, or both, of the second aqueous solution.

In one or more embodiments, a kit comprises a first container containing a first aqueous solution comprising anti-gram-negative antibiotic or salt thereof, and a second container containing a second aqueous solution comprising anti-gram-positive antibiotic or salt thereof.

In one or more embodiments, a unit dose comprises a container and a powder comprising an antibiotic or salt thereof, wherein the powder is present in an amount ranging from about 550 mg to about 900 mg.

In one or more embodiments, a unit dose comprises a container; and a powder comprising an antibiotic or salt thereof, wherein the powder is present in an amount ranging from about 150 mg to about 450 mg.

In one or more embodiments, a kit comprises a first container containing a first composition comprising an anti-gram-positive or an anti gram-negative antibiotic or salt thereof and a second container containing a second composition comprising water. The first composition and/or the second composition comprises an osmolality adjuster.

In one or more embodiments, a kit comprises a first container containing a powder comprising an anti-gram-positive antibiotic or salt thereof and a second container containing a powder comprising an anti-gram-positive antibiotic or salt thereof. A concentration, or an amount, or both, of the anti-gram-positive antibiotic or salt thereof in the first container is different from a concentration, or an amount, or both, of the anti-gram-positive antibiotic or salt thereof in the second container.

In one or more embodiments, a kit comprises a first container containing a solution comprising an anti-gram-negative antibiotic or salt thereof and a second container containing a powder comprising anti-gram-positive antibiotic or salt thereof.

In one or more embodiments, a method of administering an antibiotic formulation to a patient in need thereof comprises aerosolizing an antibiotic formulation to administer the antibiotic formulation to the pulmonary system of the patient. The antibiotic formulation has a concentration of anti-gram-negative antibiotic or salt thereof ranging from about 100 mg/ml to about 200 mg/ml.

In one or more embodiments, a method of administering an antibiotic formulation to a patient in need thereof comprises inserting a tube into a trachea of a patient. The method also comprises aerosolizing an antibiotic formulation to administer the antibiotic formulation to the pulmonary system of the patient. The antibiotic formulation consists essentially of an anti-gram-negative antibiotic or salt thereof and water.

In one or more embodiments, a method of administering an antibiotic formulation to a patient in need thereof comprises aerosolizing an antibiotic formulation to administer the antibiotic formulation to the pulmonary system of the patient. The antibiotic formulation comprises an anti-gram-positive antibiotic or salt thereof at a concentration ranging from about 0.7 to about 0.9 of the water solubility limit, at 25° C. and 1.0 atmosphere, of the anti-gram-positive antibiotic or salt thereof.

In one or more embodiments, a method of administering an antibiotic formulation to a patient in need thereof comprises aerosolizing an antibiotic formulation using a vibrating mesh nebulizer, and administering the antibiotic formulation to the pulmonary system of the patient via an endrotracheal tube, wherein the nebulizer is positioned in close proximity to the endrotracheal tube.

In one or more embodiments, a method of administering an antibiotic formulation to a patient in need thereof comprises dissolving an anti-gram-positive antibiotic or salt thereof in a solvent to form an antibiotic formulation, wherein the anti-gram-positive antibiotic or salt thereof is present at a concentration ranging from about 0.6 to about 0.9 of the water solubility limit, at 25° C. and 1.0 atmosphere, of the anti-gram-positive antibiotic or salt thereof. The method also includes aerosolizing the antibiotic formulation to administer the antibiotic formulation to the pulmonary system of the patient.

In one or more embodiments, a method of administering an antibiotic formulation to a patient in need thereof comprises dissolving an antibiotic or salt thereof in a solvent to form an antibiotic formulation. The method also includes aerosolizing the antibiotic formulation to administer the antibiotic formulation to the pulmonary system of the patient, wherein the aerosolizing is conducted within about 16 hours of the dissolving.

In one or more embodiments, a method involves forming a powder comprising an antibiotic or salt thereof. The method includes dissolving an antibiotic or salt thereof in a solvent to form a solution having a concentration ranging from about 60 mg/ml to about 120 mg/ml. The method also includes lyophilizing the solution to form the powder.

In one or more embodiments, a method involves forming a powder comprising an antibiotic or salt thereof. The method comprises dissolving an antibiotic or salt thereof in a solvent to form a solution having a volume ranging from about 4.5 ml to about 5.5 ml. The method also includes lyophilizing the solution to form the dry powder.

Therefore, in one or more embodiments, the present invention involves concentrated antibiotic formulations. The antibiotic formulations may comprise an aqueous composition of antibiotic or salt thereof being present at a concentration ranging from about 0.6 to about 0.9, such as about 0.7 to about 0.8, of the water solubility limit, at 25° C. and 1.0 atmosphere, of the antibiotic or salt thereof.

The concentration of the antibiotic, corrected for potency, in one or more embodiments, may range from about 40 mg/ml to about 200 mg/ml, such as about 60 mg/ml to about 140 mg/ml, or about 80 mg/ml to about 120 mg/ml. For example, in the case of anti-gram-negative antibiotics or salts thereof, the concentration as corrected for potency may range from about 40 mg/ml to about 200 mg/ml, such as from about 90 mg/ml to about 200 mg/ml, about 110 mg/ml to about 150 mg/ml, or about 120 mg/ml to about 140 mg/ml. As another example, in the case of anti-gram-positive antibiotics or salts thereof, the concentration as corrected for potency may range from about 60 mg/ml to about 140 mg/ml, such as about 80 mg/ml to about 120 mg/ml.

The aqueous compositions typically have a pH that is compatible with physiological administration, such as pulmonary administration. For example, the aqueous composition may have a pH ranging from about 3 to about 7, such as about 4 to about 6.

In addition, the aqueous compositions typically have an osmolality that is compatible with physiological administration, such as pulmonary administration. In one or more embodiments, the aqueous composition may have an osmolality ranging from about 90 mOsmol/kg to about 500 mOsmol/kg, such as 120 mOsmol/kg to about 500 mOsmol/kg, or about 150 mOsmol/kg to about 300 mOsmol/kg.

In one or more embodiments, the aqueous compositions are stable. For instance, in some cases, no precipitate forms in the aqueous composition when the aqueous composition is stored for 1 year, or even 2 years, at 25° C.

The potency of the antibiotic or salt thereof may range from about 500 μg/mg to about 1100 μg/mg. In one or more embodiments, the potency of anti-gram-negative antibiotics or salts thereof, such as gentamicin, typically ranges from about 500 μg/mg to about 1100 μg/mg, such as about 600 μg/mg to about 1000 μg/mg, or about 700 μg/mg to about 800 μg/mg. The potency of anti-gram-positive antibiotics or salts thereof, such as vancomycin, typically ranges from about 900 μg-mg to about 1100 μg/mg, such as from about 950 μg/mg to about 1050 μg/mg.

The chromatographic purity level of the antibiotic or salt thereof typically greater than about 80%, such as greater than about 85%, greater than about 90%, or greater than about 95%. In this regard, there is generally no major impurity greater than about 10%, such as no greater than about 5% or no greater than about 2%. For instance, the amount of heavy metals is typically less than about 0.005 wt %, such as less than about 0.004 wt %, less than about 0.003 wt %, less than about 0.002 wt %, or less than about 0.001 wt %.

In the case of gentamicin, the compositions typically have a gentamicin $C_1$ content ranging from about 25% to about 50%, such as about 30% to about 55%, about 35% to about 50%, or about 40% to about 45%, based on the total amount of gentamicin. The compositions typically have a gentamicin $C_{1a}$ content ranging from about 10% to about 35%, such as about 15% to about 30%, about 20% to about 25%, based on the total amount of gentamicin. The compositions typically have a gentamicin $C_2$ and $C_{2a}$ content ranging from about 25 wt % to about 55 wt %, such as about 30% to about 50%, about 30% to about 45%, or about 35% to about 40%, based on the total amount of gentamicin.

In embodiments of the present invention comprising amikacin, the compositions typically have an amikacin content ranging from about 25% to about 50%, such as about 30% to about 55%, about 35% to about 50%, or about 40% to about 45%, based on the total amount of amikacin.

Nearly any anti-gram-negative, anti-gram-positive antibiotic, or combinations thereof may be used. Additionally, antibiotics may comprise those having broad spectrum effectiveness, or mixed spectrum effectiveness. Antifungals, such as polyene materials, in particular, amphotericin B are also suitable for use herein. Examples of anti-gram-negative antibiotics or salts thereof include, but are not limited to, aminoglycosides or salts thereof. Examples of aminoglycosides or salts thereof include gentamicin, amikacin, kanamycin, streptomycin, neomycin, netilmicin, paramecin, tobramycin, salts thereof, and combinations thereof. For instance, gentamicin sulfate is the sulfate salt, or a mixture of such salts, of the antibiotic substances produced by the growth of *Micromonospora purpurea*. Gentamicin sulfate, USP, may be obtained from Fujian Fukang Pharmaceutical Co., LTD, Fuzhou, China. Amikacin is typically supplied as a sulfate salt, and can be obtained, for example, from Bristol-Myers Squibb. Amikacin may include related substances such as kanamicin.

Examples of anti-gram-positive antibiotics or salts thereof include, but are not limited to, macrolides or salts thereof. Examples of macrolides or salts thereof include, but are not limited to, vancomycin, erythromycin, clarithromycin, azithromycin, salts thereof, and combinations thereof. For instance, vancomycin hydrochloride is a hydrochloride salt of vancomycin, an antibiotic produced by certain strains of *Amycolatopsis orientals*, previously designated *Streptomyces orientalis*. Vancomycin hydrochloride is a mixture of related substances consisting principally of the monohydrochloride of vancomycin B. Like all glycopeptide antibiotics, vancomycin hydrochloride contains a central core heptapeptide. Vancomycin hydrochloride, USP, may be obtained from Alpharma, Copenhagen, Denmark.

In some embodiments, the composition comprises an antibiotic and one or more additional active agents. The additional active agent described herein includes an agent, drug, or compound, which provides some pharmacologic, often beneficial, effect. This includes foods, food supplements, nutrients, drugs, vaccines, vitamins, and other beneficial agents. As used herein, the terms farther include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system.

Examples of additional active agents include, but are not limited to, anti-inflammatory agents, bronchodilators, and combinations thereof.

Examples of bronchodilators include, but are not limited to, β-agonists, anti-muscarinic agents, steroids, and combinations thereof. For instance, the steroid may comprise albuterol, such as albuterol sulfate.

Active agents may comprise, for example, hypnotics and sedatives, psychic energizers, tranquilizers, respiratory drags, anticonvulsants, muscle relaxants, antiparkinson agents (dopamine antagnonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosonates, respiratory syncytial virus antibody, cystic fibrosis transmembrane regulator (CFTR) gene, deoxyribonuclease (Dnase), bactericidal/permeability increasing protein (BPI), anti-CMV antibody, 13-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafioxacin, teicoplanin, rampolanin, mideplanin, colistin, daptomycin, gramicidin, colistimethate, polymyxins such as polymyxin B, capreomycin, bacitracin, penems; penicillins including penicillinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cetamandole, cefazolin, cephaloridine, cefaclor, cefadroxil, cephaloglycin, cefuroxime, ceforanide, cefotaxime, cefatrizine, cephacetrile, cefepixne, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

The amount of antibiotic or other active agent in the pharmaceutical formulation will be that amount necessary to deliver a therapeutically or prophylactically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1 wt % to about 99 wt %, such as from about 2 wt % to about 95 wt %, or from about 5 wt % to 85 wt %, of the active agent, and will also depend upon the relative amounts of additives contained in the composition. The compositions of the invention are particularly useful for active agents that are delivered in doses of from 0.001 mg/day to 100 mg/day, such as in doses from 0.01, mg/day to 75 mg/day, or in doses from 0.10 mg/day to 50 mg/day. It is to be understood that more than one active agent may be incorporated into the formulations described herein and that the use of the term "agent" in no way excludes the use of two or more such agents.

Generally, the compositions are free of excessive excipients. In one or more embodiments, the aqueous composition consists essentially of the anti-gram-negative antibiotic, such as amikacin, or gentamicin or both, and/or salts thereof and water.

Further, in one or more embodiments, the aqueous composition is preservative-free. In this regard, the aqueous composition may be methylparaben-free and/or propylparaben-free. Still further, the aqueous composition may be saline-free.

In one or more embodiments, the compositions comprise an anti-infective and an excipient. The compositions may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts sufficient to perform their intended function, such as stability, surface modification, enhancing effectiveness or delivery of the composition or the like. Thus if present, excipient may range from about 0.01 wt % to about 95 wt %, such as from about 0.5 wt % to about 80 wt %, from about 1 wt % to about 60 wt %. Preferably, such excipients will, in part, serve to further improve the features of the active agent composition, for example by providing more efficient and reproducible delivery of the active agent and/or facilitating manufacturing. One or more excipients may also be provided to serve as bulking agents when it is desired to reduce the concentration of active agent in the formulation.

For instance, the compositions may include one or more osmolality adjuster, such as sodium chloride. For instance, sodium chloride may be added to solutions of vancomycin hydrochloride to adjust the osmolality of the solution. In one or more embodiments, an aqueous composition consists essentially of the anti-gram-positive antibiotic, such as vancomycin hydrochloride, the osmolality adjuster, and water.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination.

Exemplary protein excipients include albumins such as human serum albumin (USA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also comprise a buffer or a pH adjusting agent, typically a salt prepared from an organic acid or base. Representative buffers comprise organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, celluloses and derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), both of which are incorporated herein by reference in their entireties.

For MDI applications, the pharmaceutical formulation may also be treated so that it has high stability. Several attempts have dealt with improving suspension stability by increasing the solubility of surface-active agents in the HFA propellants. To this end U.S. Pat. No. 5,118,494, WO 91/11173 and WO 92/00107 disclose the use of HFA soluble fluorinated surfactants to improve suspension stability. Mixtures of HFA propellants with other perfluorinated cosolvents have also been disclosed as in WO 91/04011. Other attempts at stabilization involved the inclusion of nonfluorinated surfactants. In this respect, U.S. Pat. No. 5,492,688 discloses that some hydrophilic surfactants (with a hydrophilic/lipophilic balance greater than or equal to 9.6) have sufficient solubility in HFAs to stabilize medicament suspensions. Increases in the solubility of conventional non-fluorinated MDI surfactants (e.g. oleic acid, lecithin) can also reportedly be achieved with the use of co-sol vents such as alcohols, as set forth in U.S. Pat. Nos. 5,683,677 and 5,605,674, as well as in WO 95/17195. A particularly useful class of MDIs are those which use hydrofluroalkane (HFA) propellants. The HFA propellants are further particularly well suited to be used with stabilized dispersions of an active agent such as formulations and composition of aminoglycoside antibiotics. Suitable propellants, formulations, dispersions, methods, devices and systems comprise those disclosed in U.S. Pat. No. 6,309,623, the disclosure of which is incorporated by reference in its entirety. All of the aforementioned references being incorporated herein by reference in their entireties.

In one or more embodiments, the compositions comprise an aerosol having a particle or droplet size selected to permit penetration into the alveoli of the lungs, such as a mass median aerodynamic diameter, less than about 10 µm, less than about 7.5 µm, less than about 5 µm, and usually being in the range of about 0.1 µm to about 5 µm.

The compositions of the present invention may be made by any of the various methods and techniques known and available to those skilled in the art. In this regard, procedures such as lyophilizing antibiotics to make powders and/or dissolving antibiotics in solvents are known in the art.

For instance, a solution of antibiotic, e.g., amikacin sulfate or gentamicin sulfate, may be made using the following procedure. Typically, manufacturing equipment is sterilized before use. A portion of the final volume, e.g., 70%, of solvent, e.g., water for injection, may be added into a suitable container. Antibiotic or salt thereof may then be added. The antibiotic or salt thereof may be mixed until dissolved. Additional solvent may be added to make up the final batch volume. The batch may be filtered, e.g., through a 0.2 μm filter into a sterilized receiving vessel. Filling components may be sterilized before use in filling the batch into vials, e.g., 10 ml vials.

As an example, the above-noted sterilizing may include the following. A 5 liter type 1 glass bottle and lid may be placed in an autoclave bag and sterilized at elevated temperature, e.g., 121° C. for 15 minutes, using an autoclave. Similarly, vials may be placed into suitable racks, inserted into an autoclave bag, and sterilized at elevated temperature, e.g., 121° C. for 15 minutes, using an autoclave. Also similarly, stoppers may be placed in an autoclave bag and sterilized at elevated temperature, e.g., 121° C. for 15 minutes, using an autoclave. Before sterilization, sterilizing filters may be attached to tubing, e.g., a 2 mm length of 7 mm×13 mm silicone tubing. A filling line may be prepared by placed in an autoclave bag and sterilized at elevated temperature, e.g., 121° C. for 15 minutes, using an autoclave.

The above-noted filtration may involve filtration into a laminar flow work area. The receiving bottle and filters may be set up in the laminar flow work area.

The above-noted filling may also be conducted under laminar flow protection. The filling line may be unwrapped and placed into the receiving bottle. The sterilized vials and stoppers may be unwrapped under laminar flow protection. Each vial may be filled, e.g., to a target fill of 5.940 g, and stoppered. A flip off collar may be applied to each vial. The sealed vials may be inspected for vial leakage, correct overseals, and cracks.

As another example, one or more antibiotics, e.g., vancomycin, gentamicin or amikacin, and/or a salt thereof, may be prepared by lyophilizing the antibiotic to form a powder for storage. The powder is then reconstituted prior to use. This technique may be used when the antibiotic is unstable in solution.

In one or more embodiments, the powder making process may begin with forming a solution to be lyophilized. For example, an antibiotic or salt thereof, such as amikacin, gentamicin or vancomycin and/or salts thereof, may be dissolved in a solvent to form a solution having an antibiotic concentration ranging from about 80 mg/ml to about 150 mg/ml, such as about 90 mg/ml to about 130 mg/ml, or about 100 mg/ml to about 124 mg/ml. The solution to be lyophilized may have a volume ranging from about 4.5 ml to about 5.5 ml, such as about 5 ml.

In other embodiments, the powder making process may begin with forming a solution of an anti-gram negative antibiotic or salt thereof, such as amikacin or salt thereof. The antibiotic and/or salt may be dissolved in a solvent to form a solution having a concentration ranging from about 80 mg/ml to about 130 mg/ml, such as about 90 mg/ml to about 120 mg/ml, or about 100 mg/ml to about 110 mg/ml. The solution to be lyophilized may have a volume ranging from about 4.5 ml to about 5.5 ml, such as about 5 ml.

The solvent for the solution to be lyophilized may comprise water. The solution may be excipient-free. For instance, the solution may be cryoprotectant-free.

In one or more embodiments, a suitable amount (e.g., 120 g per liter of final solution) of drug substance (for example vancomycin hydrochloride) may be dissolved, e.g., in about the 75% of the theoretical total amount of water for injection under nitrogen bubbling. The dissolution time may be recorded and appearance may be evaluated.

Then, the dilution to the final volume with WFI may be carried out. Final volume may be checked. Density, pH, endotoxin, bioburden, and content by UV may be measured both before and after sterile filtration.

The solution may be filtered before lyophilizing. For instance, a double 0.22 µm filtration may be performed before filling. The filters may be tested for integrity and bubble point before and after the filtration.

Pre-washed and autoclaved vials may be aseptically filled using an automatic filling line to a target of 5 ml per vial and then partially stoppered. In process check for fill volumes may be done by checking the fill weight every 15 minutes.

The lyophilizing is generally conducted within about 72 hours, such as within about 8 hours, or within about 4 hours, of the dissolving.

In one or more embodiments, the lyophilizing comprises freezing the solution to form a frozen solution. The frozen solution is typically held at an initial temperature ranging from about −40° C. to about −50° C., such as about −45° C. During the initial temperature period, the pressure around the frozen solution is typically atmospheric pressure. The initial temperature period typically ranges from about 1 hour to about 4 hours, such about 1.5 hours to about 3 hours, or about 2 hours.

The lyophilizing may further comprise raising a temperature of the frozen solution to a first predetermined temperature, which may range from about 10° C. to about 20° C., such as about 15° C. The time for the heat ramp from the initial temperature to the first predetermined temperature generally ranges from about 6 hours to about 10 hours, such as about 7 hours to about 9 hours.

During the first predetermined temperature period, the pressure around the solution typically ranges from about 100 µbar to about 250 µbar, such as about 150 µbar to about 225 µbar. The solution may be held at the first predetermined temperature for a period ranging from about 20 hours to about 30 hours, such as from about 24 hours.

The lyophilizing may still further comprise raising a temperature of the solution to a second predetermined temperature, which may range from about 25° C. to about 35° C., such as about 30° C. During the second predetermined temperature period, the pressure around the frozen solution typically ranges from about 100 µbar to about 250 µbar, such as about 150 µbar to about 225 µbar. The solution may be held at the second predetermined temperature for a period ranging from about 10 hours to about 20 hours.

In view of the above, the lyophilization cycle may comprise a freezing ramp, e.g., from 20° C. to −45° C. in 65 minutes, followed by a freeze soak, e.g., at −45° C. for 2 hours. Primary drying may be accomplished with a heating ramp, e.g., from −45° C. to 15° C. in 8 hours, followed by a temperature hold, e.g., at 15° C. for 24 hours at a pressure of 200 µbar. Secondary drying may be accomplished with a heating ramp, e.g., from 15° C. to 30° C. in 15 minutes, followed by a temperature hold at 30° C. for 15 hours at a pressure of 200 µbar. At the end of the lyophilization cycle, the vacuum may be broken with sterile nitrogen, and the vials may be automatically stoppered.

The water content, of the powder e.g., vancomycin powder, or amikacin powder, is typically less than about 7 wt %, such as less than about 5 wt %, less than about 4 wt %, less than about 3 wt %, or less than about 2 or 1 wt %.

The chromatographic purity level of the powder, e.g., vancomycin powder, or amikacin powder, typically greater than about 80%, such as greater than about 90%, greater than about 95%, or greater than about 97%. In this regard, there is generally no major impurity greater than about 10%, such as no greater than about 7% or no greater than about 5%. For instance, the amount of heavy metals is typically less than about 0.005 wt %, such as less than about 0.004 wt %, less than about 0.003 wt %, less than about 0.002 wt %, or less than about 0.001 wt %.

The powder is capable of being reconstituted with water at 25° C. and 1.0 atmosphere and with manual agitation, in less than about 60 seconds, such as less than about 30 seconds, less than about 15 seconds, or less than about 10 seconds.

The powder typically has a large specific surface area that facilitates reconstitution. The specific surface area typically ranges from about 5 $m^2/g$ to about 20 $m^2/g$, such as about 8 $m^2/g$ to 15 $m^2/g$, or about 10 $m^2/g$ to 12 $m^2/g$.

Upon reconstitution with water, the antibiotic solution (such as vancomycin or amikacin) typically has a pH that ranges from about 2.5 to about 7, such as about 3 to about 6. Amikacin in particular may have a pH of about 5.5 to about 6.3.

In addition to use formulations for nebulization, the formulations of the present invention may be administered other routes, e.g., parenteral administration.

One or more embodiments involve methods for treating or preventing pulmonary infections, including nosocomial infections, in animals, including, especially, humans. The method generally comprises administering to an animal subject or human patient in need thereof, as an aerosol, a therapeutically or prophylactically effective amount of the antibiotic or salt thereof. Several antibiotics may be delivered in combination according to the invention, or in seriatim, in one or more embodiments, the amounts delivered to the airways, if delivered systemically in such amounts, would not be sufficient to be therapeutically effective and would certainly not be enough to induce toxicity. At the same time, in such embodiments, such amounts can result in sputum levels of antibiotic of more than about 10-100 times the minimum inhibitory concentration ("MIC").

In one particular embodiment, the pharmaceutical formulation comprises an antibiotic for administration to a ventilated patient to treat or prevent ventilator associated pneumonia (VAP) and/or hospital-acquired pneumonia (HAP) and/or community acquired pneumonia (CAP) as well as other forms of pneumonia, and other respiratory infections or conditions. Such administration is described in U.S. patent application Ser. No. 10/430,658; Ser. No. 10/430,765; and Ser. No. 10/991,092, and in U.S. Provisional Application Nos. 60/378,475; 60/380,783; 60/420,429; 60/439,894; 60/442,785; 60/682,099, and in U.S. Patent Application Publication No. 2005/021766, all of which are incorporated herein by reference in their entireties.

In one aspect, the aerosolized particles are prevented from undergoing significant hygroscopic enlargement, since particles enrobed in water will tend to condense on the walls. For instance, the method may involve reducing humidity in the ventilator circuit by a predetermined amount before nebulization begins. In this embodiment, the humidity may facilitate an MMAD of less than about 3 μm or less than about 1.5 μm. In another embodiment, each aerosol particle is delivered enrobed in a substantially anhygroscopic envelope.

Of course, embodiments can be used where diameters are greater. Moreover, in some cases, the present invention contemplates adjustments to the surface electrical charges on the particles or the walls. For example, assuming surface charge on the device is important, the present invention contemplates embodiments wherein the components of the device connectors are made of metal (or at least coated with metal). Alternatively, the components can be treated with agents (e.g. wetting agents, detergents, soaps) (o adjust surface charge.

In one aspect, the method comprises inserting an aerosol delivery end of the device within said patient's trachea to create a positioned device, the antibiotic composition is aerosolized under conditions such that the composition is delivered through said aerosol delivery end of the device to the patient, wherein the aerosol first contacts the patient's trachea (thereby bypassing the oro-pharynx). Tire method may involve administering a mixture of antibiotics and is particularly appropriate for intubated patients.

In another aspect, a method of administering comprises administering to free breathing patients by way of an aerosol generator device and/or system for administration of aerosolized medicaments such as those disclosed in U.S. Patent Application Publication Nos. 20050235987, 20050211253, 20050211245, 20040035413, and 20040011358, the disclosures of which are incorporated herein by reference in their entireties.

Such devices may deliver medicament phasically or nonphasically. Additionally or alternatively, such devices may incorporate a chamber or reservoir to accumulate and periodically dispense the aerosolized medicament. In one or more embodiments, an aerosolized medicament comprises amikacin.

In one or more embodiments, the method of administering an antibiotic formulation involves dissolving an antibiotic or salt thereof in a solvent to form an antibiotic formulation. The aerosolizing is conducted within about 16 hours, such as with about 12 hours, or within about 8 hours, of the dissolving.

In another aspect, particular with respect to "constant-flow" ventilators, the present invention contemplates limiting the delivery event to the inspiratory phase of the ventilator cycle and, if possible, at a reduced flow-rate. Thus, in one embodiment, aerosolization is actuated during (or in fixed relation to) the inspiration phase of the breathing cycle.

It is not intended that the present invention be limited to particular dosages. On the other hand, the efficiency of the aerosol systems and methods described herein permit amounts to be delivered that are too low to be generally effective if administered systemically, but are nonetheless effective amounts when administered in a suitable and pharmaceutically acceptable formulation directly to the airway. Importantly, while efficiencies can be increased, in some embodiments efficiencies are not increased at the expense of control over the dose. Thus, lower efficiencies are contemplated as preferred when delivery is more reproducible.

It is not intended that the present invention be limited to antimicrobials that only kill particular organisms. The present invention contemplates drugs and drug combinations that will address a wide variety of organisms. In one or more embodiments, the present invention contemplates drugs or drug combinations effective in the treatment of infections caused by *P. aeruginosa, S. aureus, H. influenza*, and *S. pneumoniae* and/or antibiotic-resistant strains of bacteria such as methicillin-resistant *S. aureus*, and *Acetinobacter* species, among others.

Moreover, while certain embodiments of the present invention are presented in the context of the intubated patient, other patients at risk for infection are contemplated as treatable with the compositions, methods, and devices of the present invention. For example, the elderly (particularly those in nursing homes), horses, dogs and cats in competitions (show and racing animals), animals that frequently travel (e.g., circus animals), animals in close quarters (e.g., zoos or farms), humans and animals in general are at risk for lung infections. The present invention contemplates delivery of aerosols to the trachea and/or deep lung for such individuals—both prophylactically (i.e., before symptoms) and under acute conditions (i.e., after symptoms)—wherein said aerosols comprise antimicrobials, and in particular, the antibiotic mixtures described above.

In one embodiment, the present invention contemplates administering the appropriate medication to a patient diagnosed with ARDS or chronic obstructive pulmonary disease (COPD).

One or more embodiments are directed to unit doses comprising a container and the compositions.

Examples of the container include, but are not limited to, vials, syringes, ampoules, and blow fill seal. For instance, the vial may be a colorless Type I borosilicate glass ISO 6R 10 mL vial with a chlorobutyl rubber siliconized stopper, and rip-off type aluminum cap with colored plastic cover.

The amount of the composition in the unit dose typically ranges from about 2 ml to about 15 ml, such as from about 3 ml to about 10 ml, about 4 ml to about 8 ml, or about 5 ml to about 6 ml.

The amount of the antibiotic in the unit dose, adjusted for potency, typically ranges from about 150 mg to about 900 mg, such as about 400 mg to about 750 mg. For instance, an amount of the anti-gram-negative antibiotic or salt thereof may range from about 400 mg to about 750 mg. As another example, the amount of anti-gram-positive antibiotic or salt thereof may range from about 150 mg to about 450 mg, or from about 550 mg to about 900 mg.

One or more embodiments are directed to kits. For instance, the kit may includes a first container containing a first aqueous solution comprising anti-gram-negative antibiotic or salt thereof and a second container containing a second aqueous solution comprising anti-gram-negative antibiotic or salt thereof. A concentration, or an amount, or both, of the first aqueous solution is different from a concentration, or an amount, or both, of the second aqueous solution. For instance, the amount of the first aqueous solution may range from about 2 ml to about 5 ml, and the amount of the second aqueous solution may range from about 5 ml to about 8 ml.

In one or more embodiments, the kit includes a first container containing a first aqueous solution comprising anti-gram-negative antibiotic or salt thereof. A second container contains a second aqueous solution comprising anti-gram-positive antibiotic or salt thereof. The concentrations and/or amounts of the anti-gram-negative antibiotic or salt and the anti-gram-positive antibiotic or salt may be the same or different.

In one or more embodiments, a kit includes a first container containing a first composition comprising an antibiotic or salt thereof. A second container contains a second composition comprising water. The first composition and/or the second composition comprises an osmolality adjuster.

In one or more embodiments, a kit includes a first container containing a powder comprising anti-gram-positive antibiotic or salt thereof. A second container contains a powder comprising anti-gram-positive antibiotic or salt thereof. A concentration, or an amount, or both of the anti-gram-positive antibiotic or salt thereof in the first container is different from a concentration, or an amount, or both of the anti-gram-positive antibiotic or salt thereof in the second container.

For instance, the amount of the anti-gram-positive antibiotic or salt thereof in the first container may range from about 400 mg to 600 mg. The amount of the anti-gram-positive antibiotic or salt thereof in the second container may range from about 600 mg to about 800 mg.

In another aspect, a kit may include a first container containing a solution comprising anti-gram-negative antibiotic or salt thereof. A second container may contain a powder comprising anti-gram-positive antibiotic or salt thereof. Alternatively, the anti-gram-negative antibiotic or salt thereof may be a powder, and the anti-gram-positive antibiotic or salt thereof may be a solution or dispersion. An amount of the anti-gram-positive antibiotic or salt thereof generally ranges from about 150 mg to about 900 mg.

The kits may further comprise a package, such as a bag, that contains the first container and the second container.

The kits may further comprise an aerosolization apparatus. The aerosolization apparatus may be of any type that is capable of producing respirable particles or droplets. Alternatively, the antibiotic may be dissolved in or suspended in a liquid propellant, as described in U.S. Pat. Nos. 5,225,183; 5,681,545; 5,683,677; 5,474,759; 5,508,023; 6,309,623; or 5,655,520, all of which are incorporated herein by reference in their entireties. In such cases, the aerosolization apparatus may comprise a metered dose inhaler (MDI).

Alternatively or additionally, the pharmaceutical formulation may be in a liquid form and may be aerosolized using a nebulizer as described in WO 2004/071368, which is herein incorporated by reference in its entirety, as well as U.S. Published Application Nos. 2004/0011358 and 2004/0035413, which are both herein incorporated by reference in their entireties. Other examples of nebulizers include, but are not limited to, the Aeroneb® Go or Aeroneb® Pro nebulizers, available from Aerogen, Inc. of Mountain View, Calif.; the PARI eFlow and other PARI nebulizers available from PARI Respiratory Equipment, Inc. of Midlothian, Va.; the Lumiscope® Nebulizer 6600 or 6610 available from Lumiscope Company, Inc. of East Brunswick, N.J.; and the Omron NE-U22 available from Omron Healthcare, Inc. of Kyoto, Japan.

It has been found that a nebulizer of the vibrating mesh type, such as one that that forms droplets without the use of compressed gas, such as the Aeroneb® Pro provides unexpected improvement in dosing efficiency and consistency. By generating fine droplets by using a vibrating perforated or unperforated membrane, rather than by introducing compressed air, the aerosolized pharmaceutical formulation can be introduced into the ventilator circuit without substantially affecting the flow characteristics within the circuit and without requiring a substantial re-selection of the ventilator settings. In addition, the generated droplets when using a nebulizer of this type are introduced at a low velocity, thereby decreasing the likelihood of the droplets being driven to an undesired region of the ventilator circuit. Furthermore, the combination of a droplet forming nebulizer and an aerosol introducer as described is beneficial in that there is a reduction in the variability of dosing when the ventilator uses different tidal volumes, thus making the system more universal.

Using an adaptor, device or system as disclosed in U.S. application Ser. No. 10/991,092 and/or U.S. Provisional Application No. 60/682,099, and/or U.S. Application Publication No. 2005/0217666, all of which are incorporated herein by reference in their entireties, in connection with the administration of aerosolized antibiotics offers substantial benefits. For example, when using such adaptors, substantially less pharmaceutical formulation is lost to the environment which results in a reduction in bacterial resistance against the antibiotic. In addition, the adaptors, devices or systems are able to deliver a more consistent dose which is particularly useful for antibiotic therapy.

FIG. 1A shows an embodiment of an adapter or system for aerosol delivery of medicaments, comprising a pulmonary drug delivery system ("PDDS") 100 suitable for use with the present invention. The PODS 100 may include a nebulizer 102 (also called an aerosolizer), which aerosolizes a liquid medicament stored in reservoir 104. The aerosol exiting nebulizer 102 may first enter the T-adaptor 106 that couples the nebulizer 102 to the ventilator circuit. The T-adaptor 106 is also coupled to the circuit wye 108 that has branching ventilator limbs 110 and 112.

Coupled to one of the ventilator limbs 110 or 112 may be an air pressure feedback unit 114, which equalizes the pressure in the limb with the air pressure feedback tubing 116 connected to the control module 118. In the embodiment shown, feedback unit 114 has a female connection end (e.g., an ISO 22 mm female fitting) operable to receive ventilator limb 112, and a male connection end (e.g., an ISO 22 mm male fitting) facing opposite, and operable to be inserted into the ventilator. The feedback unit may also be operable to receive a filter 115 that can trap particulates and bacteria attempting to travel between the ventilator circuit and tubing 116.

The control module 118 may monitor the pressure in the ventilator limb via tubing 116, and use the information to control the nebulizer 102 through system cable 120. In other embodiments (not shown) the control module 118 may control aerosol generation by transmitting wireless signals to a wireless control module on the nebulizer 102.

During the inhalation phase of the patient's breathing cycle, aerosolized medicament entering T-adaptor 106 may be mixed with the respiratory gases from the inspiratory ventilator limb 112 flowing to the patient's nose and/or lungs. In the embodiment shown, the aerosol and respiratory gases flow through nose piece 122 and into the nasal passages of the patient's respiratory tract.

Other embodiments of the circuit wye 108 shown in FIG. 1A are also contemplated in embodiments of the invention.

Figure 1B:
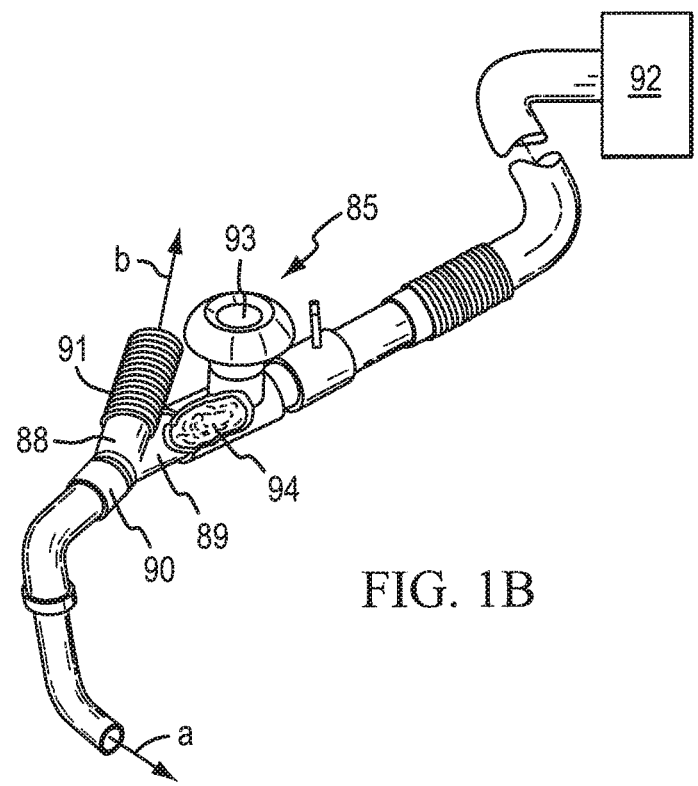
FIG. 1B shows an embodiment of a device that can be used in a pulmonary drug delivery system according to embodiments of the invention.

Referring to FIG. 1B, a nebulizer 85, which may have a top portion 93 through which liquid may be provided may be incorporated into a ventilator breathing circuit of a ventilated patient. The breathing circuit may comprise a "Y" connector 88, which may in turn have an inlet portion 89, an endotracheal tube portion 90 and an outlet portion 91. The inlet portion 89 carries air provided from the ventilator 92 toward the patient. The endrotracheal tube portion 90 of the Y connector 88 carries the incoming air to the patient's respiratory tract; this direction is represented by arrow "a". The endrotracheal tube portion 90 also carries the patient's exhalation to the outlet portion 91 of the Y connector 88, and the outlet portion may lead to an exhaust, represented by arrow "b", to remove the patient's exhalation from the system. The nebulizer 85 of the present invention aerosolization element generates an aerosol cloud 94 that remains substantially within the inlet portion 89 of the Y connector 88 when there is no inspiratory air flowing through the inlet portion, by virtue of the aerosolization element, as described above, producing a low velocity mist. In this manner, aerosol that is generated when there is no inhalation air being provided will not be carried out through the outlet portion 91 of the Y connector and lost to the ambient environment. Accordingly, a dose of aerosolized medication may be preloaded, i.e., produced and placed substantially within the inlet portion 89 prior to an inhalation phase being sent by the ventilator 92. In this manner, such medication can be swept into a patient's respiratory system at the very start of the inhalation cycle. This may be of particular benefit in the case of neonatal patients and in other instances in which only the initial blast of inhalation phase will reach the target portion of the respiratory system. In alternate embodiments, the ventilator may generate a continuous bias flow of gas through the ventilator circuit. The bias flow may push some of the aerosolized medicament through the outlet portion 91, but there is still an overall benefit from having the aerosolized medicament preloaded through the ventilator circuit.

Figures 2A, 2B:
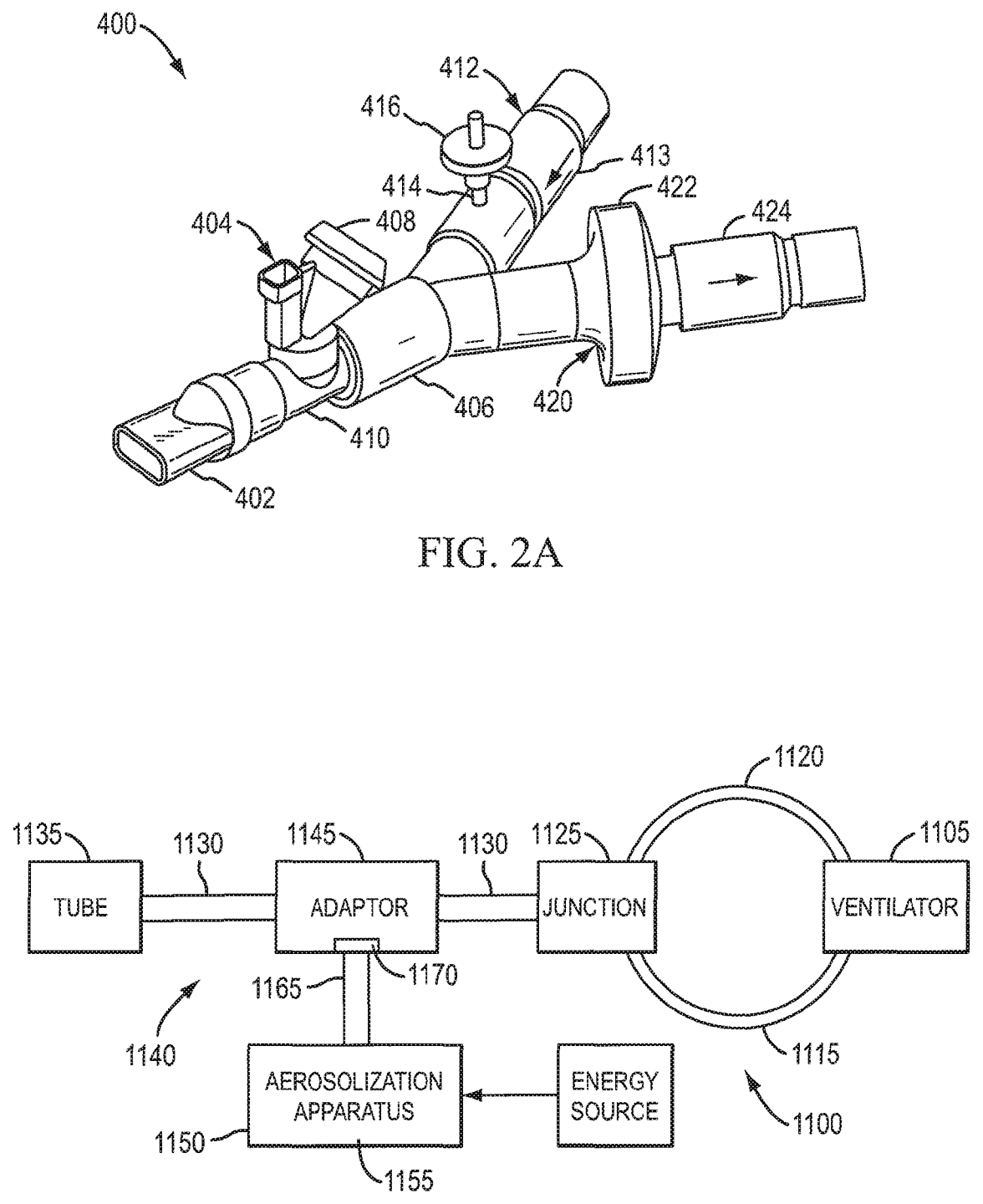

Referring now to FIG. 2A, an embodiment of an off-ventilator configuration of an adapter and/or system for pulmonary delivery is shown. In FIG. 2A, the adapter 400 is intended for off-ventilator use, and includes an endpiece 402 that is coupled to a nebulizer 404 and wye 406. The nebulizer 404 may include reservoir 408, which supplies the liquid medicament that is aerosolized into connector 410. The connector 410 can provide a conduit for the aerosolized medicament and gases to travel from the wye 406 to endpiece 402, and then into the patient's mouth and/or nose. The first wye limb 412 may be connected to a pump or source of pressurized respiratory gases (not shown), which flow through the wye limb 412 to the endpiece 402. A one-way valve 413 may also be placed in the limb 412 to prevent respired gases from flowing back into the pump or gas source. The limb 412 may also include a pressure feedback port 414 that may be connected to a gas pressure feedback unit (not shown). In the embodiment shown, a feedback, filter 416 may be coupled between the port 414 and feedback unit.

The off-ventilator adapter 400 may also include a second wye limb 420, which includes a filter 422 and one-way valve 424, through which gases may pass during an exhalation cycle. The filter 422 may filter out aerosolized medicament and infectious agents exhaled by the patient to prevent these materials from escaping into the surrounding atmosphere. The one-way valve 424 can prevent ambient air from flowing back into the adapter 400.

A general form of an aerosolized composition delivery system 1100 is shown in FIG. 2B. The aerosolized composition delivery system 1100 delivers an aerosolized composition to a portion of a user's respiratory tract, such as the user's lungs. The aerosolized composition delivery system 1100 is useful in delivering the aerosolized composition to a patient whose breathing is being assisted by a ventilator 1105 but may also be configured to be used to deliver a composition to a non-ventilated patient. The ventilator circuit 1110 is shown diagrammatically in FIG. 2B. Extending from the ventilator 1105 is an inhalation line 1115 and an exhalation line 1120. The inhalation line 1115 and the exhalation line 1120 are both composed of tubing having an airflow lumen extending therethrough. The inhalation line 1115 and the exhalation line 1120 meet at an adaptor 1145 remote from the ventilator 1105. At the adapter 1145 the lumen of the inhalation line 1115 is in communication with the lumen from the exhalation line 1120, and both lumens are in communication with a patient line 1130. The patient, line 1130 comprises a lumen that extends to the lumen of an endrotracheal or tracheotomy tube 1135, which is inserted into a patient. The tube 1135 has an opposite end that may extend into or near the lungs of the user. Accordingly, in use, oxygenated air is introduced into the inhalation line 1115 by the ventilator 1105. The oxygenated air passes through the lumen of the inhalation line 1115, into the patient line 1130, through the lumen of the tube 1135, and into the lungs of the patient. The patient then exhales, either naturally or by applying negative pressure from the ventilator, and the exhaled air passes through the tube 1135, through the patient line 1130, and through the exhalation line 1120 to the ventilator 1105. The cycle is continuously repeated to assist the patient's breathing or to entirely control the breathing of tire patient.

The adapter 1145 introduces aerosolized composition into the ventilator circuit 1110. The aerosol that is introduced by the adapter 1145 is generated by an aerosolization apparatus 1150, which comprises a reservoir for containing a composition. Thus, in one or more embodiments, aerosolization energy is supplied to the aerosolization device by an energy source 1160 to generate the aerosolized composition. The aerosolized pharmaceutical formulation passes through a passage 1165 to the adapter 1145 where it may be introduced into the ventilator circuit 1110. The aerosolization apparatus 1150 may be, for example, a jet nebulizer where the energy source is compressed air, a vibrating mesh nebulizer where the energy source is wave energy, an ultrasonic nebulizer, or a metered dose inhaler where the energy source is a propellant that boils under ambient conditions.

Examples of the adaptor 1145 for introducing the aerosolized pharmaceutical formulation are disclosed in U.S. application Ser. No. 10/991,092, filed Nov. 17, 2004, and U.S. Provisional Application No. 60/682,099, which applications are herein incorporated by reference in their entirety.

The introduction of the aerosolized pharmaceutical formulation at the adapter 1145 is advantageous in many respects over systems where the aerosol is introduced into the inhalation line 1115 or within the ventilator 1105. For example, by introducing the aerosolized pharmaceutical formulation at the adapter 1145, the ventilator circuit volume from the point of introduction to the patient's lungs is substantially reduced. Accordingly, the aerosolized pharmaceutical formulation is more concentrated and is less diffused throughout the ventilator circuit 1110. In addition, if the formulation is added in the inhalation line 1115, much of the formulation is drawn into the exhalation line 1120, further limiting the efficiency of the administration. Because of this diffusion and reduced efficiency, the consistency of dosing is difficult to control in known systems. Also, the presence of high quantities of the aerosolized pharmaceutical formulation that are not administered to the lungs of the patient may be undesirable in that much of the aerosol may be introduced into the environment where it may be inhaled by healthcare workers or others.

Therefore, the adaptor 1145 of the invention has been designed to introduce the aerosolized pharmaceutical formulation in an improved manner to increase the efficiency and/or the consistency of the dosing. The adaptor 1145 serves to reduce the amount of aerosolized pharmaceutical formulation that is drawn into the exhalation line 1120 of the ventilator circuit 1120.

The adaptors of the present invention when used in a ventilator circuit are often able to reproducibly and efficiently deliver pharmaceutical formulation. For instance, the present invention is typically able to reproduce the delivered dose within about =10%, ±8%, ±6%, ±4%, ±2%, or ±1%, of the total nominal dose. The present invention is often able to achieve a delivered efficiency of at least about 30%, such as at least about 40%, at least about 50%, at least about 60%, at least about 70%, at least about 80%, or at least about 90%.

The adaptor of the present invention typically has minimal impact on the patient to ventilator interface. The minimal impact allows the ventilator to react more efficiently to the patient. The adaptor and valves are arranged so that at an air flow rate of 60 L/min, the pressure drop between the first end and the second end of the adaptor is often less than about 50 cm $H_2O$, such as less than about 30 cm $H_2O$, less than about 5 cm $H_2O$, less than about 4 cm $H_2O$, less than about 3 cm $H_2O$, less than about 2 $H_2O$, less than about 1 cm $H_2O$, less than about 0.5 cm $H_2O$, or less than about 0.1 cm $H_2O$, and may range from about 0.05 cm $H_2O$ to about 10 cm $H_2O$, about 1 cm $H_2O$ to about 5 cm $H_2O$, or about 2 cm $H_2O$ to about 4 cm $H_2O$. At an air flow rate of 30 L/min, the pressure drop between the first end and the second end of the adaptor is typically ranges from about 1 cm $H_2O$ to about 2 cm $H_2O$.

The adaptor may be made of a transparent, translucent, or opaque material. Using a transparent material is advantageous because the user can visually inspect the functioning of the adaptor. Examples of materials for the adaptor include, but are not limited, to polymers, such as polypropylene, SAN (styrene acrylonitrile copolymer), ABS (acrylonitrile-butadiene-styrene), polycarbonate, acrylic polysulfone, K-Resin® styrene-butadiene-copolymer (available from Chevron Phillips Chemical), polyethylene, PVC (polyvinyl chloride), polystyrene, and the like.

For vibrating mesh nebulizers, such as the Aeroneb Pro and the PARI eFlow, reproducible administrations can result from smaller first channel volumes. It has been determined, for example, that the first channel volume for an adaptor 1145 used with a vibrating mesh nebulizer may be any volume greater than about 10 ml, such as from about 10 ml to about 1000 ml, about 50 ml to about 200 ml, or about 90 ml. Both the stored, volume and valving affect the performance of the present invention.

Additional examples of devices and methods are disclosed in U.S. patent application Ser. No. 11/436,329, "Valves, Devices, and Methods for Endobronchial Therapy," filed May 18, 2006, which is incorporated herein by reference in its entirety.

The present invention is not limited to any precise desired outcome when using the above-described compositions, devices, and methods. However, it is believed that the compositions, devices, and methods of the present invention may result in a reduction in mortality rates of intubated patients, a decrease in the incidence of resistance (or at least no increase in resistance) because of the reduced systemic antibiotic exposure and elevated exposure at the targeted mucosal surface of the lung caused by local administration. As noted above, it is contemplated that the compositions, devices, and methods of the present invention are useful in the treatment of pneumonia (and may be more effective than systemic treatment—or at the very least, a useful adjunct). It is believed that related infections may also be prevented or reduced (e.g., prevention of sepsis, suppression of urinary tract infections, etc.)

Of course a reduced use of systemic antibiotics because of the efficacy of the compositions, devices, and methods of the present invention may result in reduced cost, reduced time on IV lines, and/or reduced time on central lines). Moreover, such a reduction should reduce antibiotic toxicity (as measured by reduced incidence of diarrhea and *C. difficile* infection, better nutrition, etc.)

It is believed that the compositions, devices, and methods of the present invention will locally result in a reduction of the ET/Trach tube biofilm. This should, in turn, get rid of secretions, decrease airway resistance, and/or decrease the work of breathing. The latter should ease the process of weaning the patient off of the ventilator.

The present invention contemplates specific embodiments that can replace commonly used elements of a ventilator system. In one or more embodiments, the present invention contemplates an adapter attachable to a ventilator circuit and to an endrotracheal tube, wherein the adaptor comprises an aerosol generator. While not limited to any precise desired outcome, it is contemplated that the adapter with integral generator will reduce the effects of the ventilator on all conventional aerosol systems (jet, ultrasonic and MDI), and at the same time enhance the positive qualities of a device like the Aerogen™ pro. Again, while not limited to any precise desired outcome, it is contemplated that the adapter with integral generator will (1) reduce variability in delivery (reduced effects of humidification, bias flow, continuous vs breath-actuated) so as to achieve the same delivery (no matter what commercial ventilator system is used); (2) allow for maximal effects of breath actuation; and (3) allow for maximal effect to enhanced nebulizer efficiency using nebulizers having no dead volume.

The present invention is not limited to the precise configuration or nature of the circuit. In one embodiment, said circuit is a closed circuit. In another embodiment, said circuit is an open circuit.

Again, the present invention is not limited to particular vent configurations. In one embodiment, said inspiratory and said expiratory lines are connected to a mechanical ventilator. In one embodiment, said mechanical ventilator controls a breathing cycle, said cycle comprising an inspiration phase. In one embodiment, the aerosol is administered during the inspiration phase of the breathing cycle.

Although the present invention has been described in considerable detail with regard to certain versions thereof, other versions are possible, and alterations, permutations and equivalents of the version shown will become apparent to those skilled in the art upon a reading of the specification and study of the drawings. For example, the relative positions of the elements in the aerosolization device may be changed, and flexible parts may be replaced by more rigid parts that are hinged, or otherwise movable, to mimic the action of the flexible part. In addition, the passageways need not necessarily be substantially linear, as shown in the drawings, but may be curved or angled, for example. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

The foregoing description will be more fully understood with reference to the following Examples. Such Examples, are, however, merely representative of methods of practicing one or more embodiments of the present invention and should not be read as limiting the scope of the invention.

Example 1

This Example involves determining the solubility of gentamicin sulfate in water and saline. The required strengths were initially set at 20 mg/ml, 40 mg/ml, and up to 200 mg/ml.

Water Solubility Determinations

Solubility in water was determined via visual assessment. Osmolality and pH were also determined.

The batch size of all the solutions manufactured for the solubility determination studies was 10 ml. The method of manufacture consisted of weighing the appropriate amount of gentamicin sulfate and then taking to final volume with water. It was noted that especially for higher concentrations, the solution was first shaken by hand and then placed on a magnetic stirrer to ensure complete dissolution.

Table 1 lists the pH and osmolality values obtained for solutions of gentamicin sulfate in water for injection (WFI) with concentrations ranging from 20 mg/ml to 400 mg/ml.

TABLE 1

Test Matrix for Gentamicin Solution in WFI

| Active Concentration (mg/ml) | Weight of Gentamicin Sulfate Dispensed(*) (mg/ml) | pH | Osmolality (mOsmol/kg) |
|---|---|---|---|
| 20 | 34 | 4.81 | 61 |
| 40 | 68 | 4.72 | 101 |
| 80 | 136 | 4.92 | 197 |
| 120 | 204 | 4.93 | 275 |
| 200 | 340 | 5.01 | 524 |
| 250 | 425 | 5.06 | 1178 |
| 300 | 510 | 5.13 | 2013 |
| 350 | 595 | 5.20 | NR |
| 400 | 680 | 5.26 | NR |

(*)Activity of gentamicin sulfate = 58.8%, so conversion factor = 1.701
NR: No result, sample did not freeze As seen in Table 1, all the solutions had a pH that was higher than 4, which is considered to be acceptable for drug delivery to the lungs. However, with regard to osmolality readings, doses greater than 200 mg/ml exceeded the targeted range.

Gentamicin Sulfate in 0.9% Saline Solution

The solubility, pH, and osmolality of gentamicin sulfate solutions prepared with 0.9% saline solution were determined. The solubility was determined by visual assessment. Only three concentrations of gentamicin were investigated (20, 40, and 80 mg/ml).

Table 2 lists the parameters measured for gentamicin solutions and the observations recorded during manufacture.

TABLE 2

Osmolality and pH of Gentamicin Sulfate in 0.9% Saline

| Active Concentration (mg/ml) | Weight of Gentamicin Sulfate Dispensed (mg/ml) | pH | Osmolality (mOsmol/kg) |
|---|---|---|---|
| 20 | 34 | 4.94 | 318 |
| 40 | 68 | 4.72 | 353 |
| 80 | 136 | 4.82 | 445 |

Example 2

This Example involves developing the freeze-drying cycle for the clinical manufacture of the Vancomycin HCl lyophilisate. A 120 mg, 240 mg, and 480 mg of Vancomycin HCl/vial strength were investigated.

Materials/Equipment

Materials

Vancomycin hydrochloride, USP, Alpharma—Denmark
ISO 6R clear type I glass vials, Nuova Ompi—Italy
20 mm freeze-drying stoppers, West Pharmaceutical Service-USA
20 mm flip-off caps, Capsulit S.p.A.—Italy
13 mm freeze-drying stoppers, West Pharmaceutical Service-USA
13 mm flip-off caps, West Pharmaceutical Service-USA Equipment Glassware for Vancomycin solution before and after filtration (bottles).
Pressure vessel, Sartorius—Germany
Balance to check the filling weight (10 mg sensitivity), Sartorius—Germany
Digital pH meter, Mettler Toledo—Switzerland
Karl Fischer automatic titrator DL38, Mettler Toledo—Switzerland.
0.22 μm sterilizing PVDF filter, Pall
Manual doser, Hirschmann
Isolator, E. Co. Tec—Italy
Lyophilizer, BOC Edwards Lyoflex 04 (or Minifast 8000) with the following characteristics: 0.4 m2 (or 0.8 m2) shelf surface; temperature range −50° C. to 50° C. PT 100 temperature probes; Pirani gauge for vacuum monitoring; coil condenser with ice capacity of 8 kg; condenser coil inlet temperature to −60° C., stainless steel trays with a thickness of about 2 mm; semiautomatic crimping machine (Flexseal—Denmark)
DSC Pyris Diamond—USA Composition Solubility Study The solubility of the Vancomycin HCl has been evaluated in order to establish a suitable formulation to obtain a final lyophilised product which matches all the criteria required by its use as pharmaceutical form.

The solubility coupled with a pH evaluation of Vancomycin HCl solutions at different concentration was the first step to focus the suitable final formulation for a better development of the lyophilization cycle.

A saturated solution of Vancomycin HCl in water for injection was prepared by adding under stirring the active agent to the solvent.

At first, the solution was clear with the solid suspended as an agglomerate; after the solid worked as crystallization nucleus and a new precipitation occurred; so the solutions became white and more viscous because the solid partially swells.

Suspension was stirred for 48 h in order to reach the equilibrium conditions for the dissolution.

Suspensions was filtered first through a paper filter and then through a 0.45 μm PVDF filter discarding the first drops of solution which could have been diluted because of the binding of the product to the membrane.

The resulting solution obtained after the two filtrations was stored at 2-8° C. in order to evaluate if precipitation of the solid occurs.

The filtrated solutions of Vancomycin HCl in water coming from the respective saturated solutions, was diluted to reach a final concentration which gave an Abs value λ=280 nm included into the calibration curve.

Each diluted solution was analysed in triplicate with UV at λ=280 nm. For each solution the absorbances have been mediated and the final value has been substituted in the respective calibration curve equation to calculate the concentration.

The maximum solubility of Vancomycin HCl in water is 140.9 mg/mL.

pH of Vancomycin HCl Solution in Water

Besides the solubility evaluation it was also measured the pH and density of Vancomycin HCl solutions at different concentrations which could have been taken into account for the development of the formulation and of the lyophilization cycle.

| Solution Concentration (mg/mL) | pH | Density (g/mL) |
|---|---|---|
| 140.8 | 3.4-3.5 | 1.046 |
| 130.5 | 3.5-3.7 | 1.042 |
| 120.26 | 3.6-3.8 | 1.037 |
| 110.16 | 3.7-3.9 | 1.034 |
| 100.12 | 3.8-4.1 | 1.027 |

The pH varied within a restricted range for each concentration and the overall pH within 140 mg/mL and 100 mg/mL was stable around the acid value.

Formulation

Vancomycin hydrochloride was dissolved in water for injection to form 100 mg/ml formulations in 1.00 ml and 1.20 ml amounts, as shown below.

| | Quantity | |
|---|---|---|
| Ingredients | Amount/ml | Amount/Unit |
| Vancomycin HCl | 100.00 | 120.00 mg |
| Water for injection | to 1.00 ml | to 1.20 ml |

Vancomycin hydrochloride was also dissolved in water for injection to form 120 mg/ml formulations in 1.00 ml, 2.00 ml, and 4.00 ml amounts, as shown below.

| | Quantity | | | |
|---|---|---|---|---|
| | | Amount/Unit | | |
| Ingredients | Amount/ml | 120 mg/vial | 240 mg/vial | 480 mg/vial |
| Vancomycin HCl | 120.0 | 120.00 mg | 240.00 mg | 480.00 mg |
| Water for injection | to 1.00 ml | to 1.00 ml | to 2.00 ml | to 4.00 ml |

DSC Studies

DSC was performed on the ready to fill solution with a concentration of 100 mg/ml and 120 mg/ml.

The DSC runs were performed by cooling the samples to −50° C. at a cooling rate of 1° C./min, and by heating them back to 20° C. at different scan rates after a period of few minutes of isothermal step.

Samples amount ranged approximately from 1 to 3 mg.

All the peaks corresponding to the detected thermal events were calculated as onset temperature.

The DSC studies showed that there was a main event of crystallization during freezing and that there is no evidence of smaller crystallization events. These phenomena seem to indicate an absence of amorphous phase during freezing and a complete retention of crystalline structure by vancomycin, as confirmed by the lack of glass transitions events during the heating steps in all cases.

As expected, crystallization peak was displaced to lower temperatures when increasing the weight of the sample or the concentration of the solution.

However no significant difference was detected among the different concentrations.

Detected differences are more linked to the internal variability of samples.

A freezing end temperature of −45° C. as well as a freezing rate of 1° C./min was chosen to ensure a full crystalline state of the Vancomycin HCl during freezing.

Since the maximum allowable product temperature during initial primary drying was −25° C., the pressure during primary drying was within ¼ to ½ of the vapor pressure of ice at −25° C. Vapor of ice at −25° C. is 630 µbar. The average of the thresholds, 230 µbar, was selected as the maximum allowed chamber pressure for primary drying.

Manufacturing Process

Water for injection was weighed out in a glass container on calibrated balances.

Vancomycin HCl was added under stirring; the solution was agitated until vancomycin was completely dissolved and the dissolution time was recorded.

Then, water for injection was added until the required final amount was reached.

On the final solution, pH and density were measured and appearance was evaluated.

The solution was filtered through a 0.22 µm PVDF membrane.

The vials were washed with distilled water and dried in an oven at 120° C. for 2 h.

The filling was performed by mass and the in process controls were carried out by weighing the filled vials every 20 vials.

After lyophilization the following analyses were performed on the final product:

water content by Karl Fischer titration; appearance of the cake, reconstitution time, appearance/clarity, pH after reconstitution.

RP-HPLC was run to confirm processing did not influence purity of vancomycin.

Twenty (20) ml of reconstituted drug product were passed through the sterility testing membrane to confirm formulation compatibility.

Example 2A

After evaluation of the DSC results, the following lyophilization cycle nominal parameters were planned for use on the 100 mg/ml solution:

| Step No | Description | Temperature (° C.) | Pressure | Time (hh:mm) |
|---|---|---|---|---|
| 1 | Load | 20 | Atmospheric | NA |
| 2 | Product freezing | 20→−45 | Atmospheric | 01:05 |
| 3 | Freeze soak time | −45 | Atmospheric | 03:00 |
| 4 | Evacuation | −45 | 100 µbar | 00:01 |
| 5 | Primary drying | −45→ 10 | 100 µbar | 08:00 |
| 6 | Primary drying | 10 | 100 µbar | 14:00 |
| 7 | Secondary drying | 10 → 40 | 100 µbar | 00:30 |
| 8 | Secondary drying | 40 | 100 µbar | 09:00 |
| 9 | Pre-aeration | | 0.95 bar | NA |

-continued

| Step No | Description | Temperature (° C.) | Pressure | Time (hh:mm) |
|---|---|---|---|---|
| 10 | Stoppering | | 0.95 bar | NA |
| 11 | Aeration | | Atmospheric | NA |
| | | | Total length | 35:36 |

The freezing soak and primary drying times were shortened with respect to the set lyophilization program.

Actually, the product reached −45° C. after 80 minutes of the freezing soak step. It was been kept at −45° C. one hour more and then the vacuum was pulled in the chamber to start primary drying.

During step 6 (primary drying), all the product temperature probes reached the temperature of the shelves (10° C.) after 450 minutes.

The product was left at 10° C. for 1 hour; afterwards several pressure raise tests were performed to evaluate the sublimation rate. The positive results of these tests allowed to start heating to 40° C. for secondary drying. Step 6 lasted 510 minutes instead of 840 minutes.

Total length of the cycle was 29 hours.

The cake had a cohesive structure that prevented loss of friable material from the container during sublimation; lyophilised product was not really elegant because of some cracks in the cake (see the picture 1).

Example 2B

In this Example involving 100 mg/ml solution, 6R vials were used. In this regard, twenty (20) mm neck vials enable a faster sublimation than the 13 mm neck vials.

An intermediate step at 0° C. during the primary drying was inserted to have slower water vapor flow during sublimation. In this way less cracks in the lyophilization cake were observed.

The secondary drying temperature was reduced from 40° C. to 30° C. according a client's request.

Final primary drying temperature was increased from 10° C. to 15° C. to try to maintain the total length of the cycle to about 29 hours.

The nominal lyophilization parameters for this Example were:

| Step No | Description | Temperature (° C.) | Pressure | Time (hh:mm) |
|---|---|---|---|---|
| 1 | Load | 20 | Atmospheric | NA |
| 2 | Product freezing | 20→−45 | Atmospheric | 01:05 |
| 3 | Freeze soak time | −45 | Atmospheric | 03:00 |
| 4 | Evacuation | −45 | 100 μbar | 00:01 |
| 5 | Primary drying | −45→ 0 | 100 μbar | 04:00 |
| 6 | Primary drying | 0 | 100 μbar | 02:00 |
| 7 | Primary drying | 0 → 15 | 100 μbar | 02:00 |
| 8 | Primary drying | 15 | 100 μbar | 10:00 |
| 9 | Secondary drying | 15 → 30 | 100 μbar | 00:15 |
| 10 | Secondary drying | 30 | 100 μbar | 09:00 |
| 11 | Pre-aeration | | 0.95 bar | NA |
| 12 | Stoppering | | 0.95 bar | NA |
| 13 | Aeration | | Atmospheric | NA |

The lower secondary drying temperature did not allow the product to maintain a relatively low residual moisture. The overall average value was 3.61 wt %, while the average moisture content of previous batch was 1.71 wt %.

Example 2C

In this Example involving 100 mg/ml solution, the pressure in the chamber was increased from 100 μbar to 200 μbar; a higher pressure will favor the thermal exchanges at the gas/product interface and the thermal conductivity from the shelf to the tray. The bigger amount of heat transported to the product should result in a rise of product temperature and consequently in a faster ice sublimation.

Furthermore, after the evaluation of the lyophilization printout, 4 hours were cut from the primary drying and added the secondary drying step.

This Example involved the following nominal parameters:

| Step No | Description | Temperature (° C.) | Pressure | Time (hh:mm) |
|---|---|---|---|---|
| 1 | Load | 20 | Atmospheric | NA |
| 2 | Product freezing | 20→−45 | Atmospheric | 01:05 |
| 3 | Freeze soak time | −45 | Atmospheric | 03:00 |
| 4 | Evacuation | −45 | 200 μbar | 00:01 |
| 5 | Primary drying | −45→ 0 | 200 μbar | 04:00 |
| 6 | Primary drying | 0 | 200 μbar | 02:00 |
| 7 | Primary drying | 0 → 15 | 200 μbar | 02:00 |
| 8 | Primary drying | 15 | 200 μbar | 06:00 |
| 9 | Secondary drying | 15 → 30 | 200 μbar | 00:15 |
| 10 | Secondary drying | 30 | 200 μbar | 13:00 |
| 11 | Pre-aeration | | 0.95 bar | NA |
| 12 | Stoppering | | 0.95 bar | NA |
| 13 | Aeration | | Atmospheric | NA |
| | | | Total length | 31:21 |

Secondary drying was shortened from the programmed 780 minutes to 450 minutes. Actually, the product temperature matched the shelf temperature very soon due to the better heat exchange by drying at 200 μbar.

The total length of the cycle was 24.5 hours.

Average moisture content was 1.82 wt %.

The lyophilization product still showed cracks in the cake.

Example 2D

This Example involves a filling solution of 120 mg/ml to allow doses of 120 mg, 240 mg, and 480 mg per vial.

All three fill volumes were lyophilized using the cycle for the larger fill sample without paying attention to a possible over drying of the lower fill volume samples.

The vancomycin 120 mg/mL filling solution was investigated by performing a scansion with the differential calorimeter, and it has been verified that the main thermal events were very close to the ones detected on the 100 mg/mL filling solution.

This meant that the same lyophilization cycle conditions were used for the 100 mg/mL could be applied to the 120 mg/mL.

New holding time studies were also performed on the 120 mg/mL concentration. The new cycle was tested on the 480 mg/vial presentation that had the higher fill volume: 4 mL/vial.

The following nominal parameters were tested:

| Step No | Description | Temperature (° C.) | Pressure | Time (hh:mm) |
|---|---|---|---|---|
| 1 | Load | 20 | Atmospheric | NA |
| 2 | Product freezing | 20→−45 | Atmospheric | 01:05 |

| Step No | Description | Temperature (° C.) | Pressure | Time (hh:mm) |
|---|---|---|---|---|
| 3 | Freeze soak time | −45 | Atmospheric | 02:00 |
| 4 | Evacuation | −45 | 200 µbar | 00:01 |
| 5 | Primary drying | −45→ 0 | 200 µbar | 04:00 |
| 6 | Primary drying | 0 | 200 µbar | 02:00 |
| 7 | Primary drying | 0 → 15 | 200 µbar | 02:00 |
| 8 | Primary drying | 15 | 200 µbar | 24:00 |
| 9 | Secondary drying | 15 → 30 | 200 µbar | 00:15 |
| 10 | Secondary drying | 30 | 200 µbar | 15:00 |
| 11 | Pre-aeration | | 0.95 bar | NA |
| 12 | Stoppering | | 0.95 bar | NA |
| 13 | Aeration | | Atmospheric | NA |
| | | | Total length | 50:21 |

An overall average moisture content value of 0.97 wt % was found by Karl Fisher titration.

Example 2E

Following the evaluation of the product temperature profile versus the shelves temperature, the following run was cut three to four hours in the primary drying step and four hours in the secondary drying.

The 120 mg and the 240 mg units were placed in the lyophilizer during the 480 mg cycle to check if over drying will affect the chemical stability of the 120 mg and 240 mg vials.

The average residual moisture was 0.97 wt % for the 4 ml fill, 1.23 wt % for the 2 ml fill, and 1.34 wt % for the 1 ml.

The lyophilization cycle had a total length of nearly 42 hours.

| Step No | Description | Temperature (° C.) | Pressure | Time (hh:mm) |
|---|---|---|---|---|
| 1 | Load | 20 | Atmospheric | NA |
| 2 | Product freezing | 20→−45 | Atmospheric | 01:05 |
| 3 | Freeze soak time | −45 | Atmospheric | 02:00 |
| 4 | Evacuation | −45 | 200 µbar | 00:01 |
| 5 | Primary drying | −45→ 0 | 200 µbar | 04:00 |
| 6 | Primary drying | 0 | 200 µbar | 02:00 |
| 7 | Primary drying | 0 → 15 | 200 µbar | 02:00 |
| 8 | Primary drying | 15 | 200 µbar | 20:00 |
| 9 | Secondary drying | 15 → 30 | 200 µbar | 00:15 |
| 10 | Secondary drying | 30 | 200 µbar | 11:00 |
| 11 | Pre-aeration | | 0.95 bar | NA |
| 12 | Stoppering | | 0.95 bar | NA |
| 13 | Aeration | | Atmospheric | NA |
| | | | Total length | 42:21 |

All three presentations had cake with a very cohesive structure even if some cracks were present.

Analytical Results

In Process Controls

| | | Results | | | | |
|---|---|---|---|---|---|---|
| Process step | Analytical Test | 2A | 2B | 2C | 2D | 2E |
| Formulated Bulk solution | pH | 3.90 | 3.86 | 3.83 | 3.69 | 3.72 |
| | Density (g/mL) | 1.027 | 1.028 | 1.030 | 1.0394 | 1.0389 |

Tests on Freeze-Dried Drug Product

| | | Results | | | | |
|---|---|---|---|---|---|---|
| Process step | Analytical Test | 2A | 2B | 2C | 2D | 2E |
| Final Lyophilizate | Water content by KF [% w/w] | 1.71 | 3.61 | 1.82 | 0.97 | See below |
| | Visual aspect of the cake | Conform | Conform | Conform | Conform | Conform |
| | Reconstitution time | ~30" | ~30" | ~30" | ~5" | See below |
| | Appearance of reconstituted solution (water, 50 mg/ml) | Conform | Conform | Conform | Conform | Conform |
| | pH | 3.54 | 3.53 | 3.54 | 3.30 | See below |
| | % Vancomycin B HCl [HPLC] | 93.0 | 92.9 | 92.9 | 92.0 | See below |
| | % impurities | 7.0 | 7.2 | 6.9 | 8.0 | See below |

Moisture Content (K.F.) [wt %]

| | Results | | | | 2E | | |
|---|---|---|---|---|---|---|---|
| Sample | 2A | 2B | 2C | 2D | 120 mg | 240 mg | 480 mg |
| Front sample | 2.06 | 3.54 | 1.92 | 1.02 | 1.41 | 1.26 | 0.96 |
| Middle sample | 1.40 | 3.12 | 1.80 | 1.01 | 1.27 | 1.15 | 0.97 |
| Back sample | 1.68 | 4.17 | 1.74 | 0.92 | 1.27 | 1.27 | 0.97 |
| Average | 1.71 | 3.61 | 1.82 | 0.97 | 1.34 | 1.23 | 0.97 | pH

| | Results | | | | 2E | | |
|---|---|---|---|---|---|---|---|
| Sample | 2A | 2B | 2C | 2D | 120 mg | 240 mg | 480 mg |
| Front sample | 3.49 | 3.54 | 3.56 | 3.32 | 3.36 | 3.39 | 3.31 |
| Middle sample | 3.57 | 3.52 | 3.52 | 3.29 | 3.36 | 3.38 | 3.33 |
| Back sample | 3.58 | 3.52 | 3.54 | 3.30 | 3.37 | 3.39 | 3.31 |
| Average | 3.54 | 3.53 | 3.54 | 3.30 | 3.36 | 3.39 | 3.32 |

% Content Vancomycin B Hydrochloride (% VMB)

| Sample | Reference Std. Vancomycin | 2A | 2B | 2C | 2E | 2D | |
|---|---|---|---|---|---|---|---|
| Front sample | 93.7 | 92.9 | 92.9 | 92.9 | 93.7 | 120 mg | 91.3 |
| | | | | | | 240 mg | 91.6 |
| | | | | | | 480 mg | 92.5 |
| Middle sample | | 93.0 | 93.0 | 93.0 | 92.1 | 120 mg | 91.8 |
| | | | | | | 240 mg | 91.7 |
| | | | | | | 480 mg | 92.1 |
| Back sample | | 93.1 | 93.0 | 93.0 | 91.9 | 120 mg | 92.1 |
| | | | | | | 240 mg | 91.2 |
| | | | | | | 480 mg | 91.8 |
| Average | | 93.0 | 92.9 | 92.9 | 92.0 | 120 mg | 91.7 |
| | | | | | | 240 mg | 91.5 |
| | | | | | | 480 mg | 92.1 |
| Standard Dev. | | 0.104 | 0.0327 | 0.0327 | 0.108 | 120 mg | 0.415 |
| | | | | | | 240 mg | 0.261 |
| | | | | | | 480 mg | 0.343 |
| % RSD | | 0.112 | 0.0352 | 0.0352 | 0.117 | 120 mg | 0.453 |
| | | | | | | 240 mg | 0.285 |
| | | | | | | 480 mg | 0.372 |

Related Substances (% Impurities)

| Sample | Reference Std. Vancomycin | 2A | 2B | 2C | 2D | 2E | |
|---|---|---|---|---|---|---|---|
| Front sample | 6.3 | 7.1 | 7.2 | 6.9 | 6.3 | 120 mg | 8.8 |
| | | | | | | 240 mg | 8.4 |
| | | | | | | 480 mg | 7.5 |
| Middle sample | | 7.1 | 7.3 | 6.9 | 7.9 | 120 mg | 8.2 |
| | | | | | | 240 mg | 8.3 |
| | | | | | | 480 mg | 7.9 |
| Back sample | | 6.9 | 7.1 | 7.0 | 8.1 | 120 mg | 7.9 |
| | | | | | | 240 mg | 8.8 |
| | | | | | | 480 mg | 8.3 |
| Average | | 7.0 | 7.2 | 6.9 | 8.0 | 120 mg | 8.3 |
| | | | | | | 240 mg | 8.5 |
| | | | | | | 480 mg | 7.9 |
| Standard Dev. | | 0.12 | 0.09 | 0.013 | 0.11 | 120 mg | 0.42 |
| | | | | | | 240 mg | 0.26 |
| | | | | | | 480 mg | 0.42 |
| % RSD | | 1.7 | 1.2 | 0.23 | 1.3 | 120 mg | 5.0 |
| | | | | | | 240 mg | 3.1 |
| | | | | | | 480 mg | 5.3 |

Reconstitution Time

Reconstitution time measurement was carried out adding:
1.0 mL of WFI to the 120 mg/vial strength
2.0 mL of WFI to the 240 mg/vial strength
4.0 mL of WFI to the 480 mg/vial strength The observed reconstitution time on the product of Example 2E was quite short relative to all the tested vials; about 10 seconds were needed to completely reconstitute the 120 mg freeze-dried drug product; 10 to 15 seconds were needed to completely reconstitute the 240 mg/vial presentation, while about 20 seconds were needed to completely reconstitute the 480 mg units.

The reconstituted solution had a clear, light pinkish appearance and was particle free.

Compatibility with Sterility Testing Membrane 20 mL of reconstituted drug product were passed through the sterility testing membrane to confirm the formulation compatibility.

The solution passed through the filter membrane, and 17 ml of the 20 ml were collected below the membrane.

Example 3

Summary

This Example involves a freeze-drying cycle for a 600 mg of Vancomycin HCl/vial strength.

Materials/Equipment

Materials

Vancomycin hydrochloride, USP, Alpharma—Denmark
ISO 6R clear type I glass vials, Nuova Ompi—Italy
20 mm freeze-drying stoppers, West Pharmaceutical Service-USA
20 mm flip-off caps, Capsulit S.p.A.—Italy
13 mm freeze-drying stoppers, West Pharmaceutical Service-USA
13 mm flip-off caps, West Pharmaceutical Service-USA Equipment Glassware for Vancomycin solution before and after filtration (bottles).
Pressure vessel, Sartorius—Germany
Balance to check the filling weight (10 mg sensitivity), Sartorius—Germany Digital pH meter, Mettler Toledo—Switzerland
Karl Fischer automatic titrator DL38, Mettler Toledo—Switzerland
0.22 μm sterilizing PVDF filter, Pall
Semiautomatic filling machine, Flexicon PF6—Denmark
Isolator, E. Co. Tec—Italy
  Lyophilizer, BOC Edwards Lyoflex 04 (or Minifest 8000) with the following characteristics: 0.4 m² (or 0.8 m²) shelf surface, shelf temperature range was −50° C. to +50° C., PT 100 temperature probes, Pirani gauge for vacuum monitoring, coil condenser with ice capacity of 8 kg, condenser coil inlet, temperature arrives to −60° C. stainless steel trays with a thickness of about 2 mm
  Semiautomatic crimping machine, Flexseal—Denmark Formulation Vancomycin hydrochloride was dissolved in water for injection to form a 120 mg/ml formulation, as shown below.

| Ingredients | Quantity | |
|---|---|---|
| | Amount/ml | Amount/Unit |
| Vancomycin HCl | 120.00 | 600.00 mg |
| Water for injection | to 1.00 ml | to 5.00 ml |

Manufacturing Process

Water for injection was weighed out in a glass container on calibrated balances.

Vancomycin HCl was added under stirring; the solution was agitated until vancomycin was completely dissolved and the dissolution time was recorded.

Then, water for injection was added until the required final amount was reached.

On the final solution, pH and density were measured and appearance was evaluated.

The solution was filtered through a 0.22 μm PVDF membrane.

The vials were washed with distilled water and dried in an oven at 120° C. for 2 h.

The filling was performed by mass and the in process controls were carried out by weighing the filled vials every 20 vials.

After lyophilization the following analyses were performed on the final product:
  water content by Karl Fischer titration;
  appearance of the cake,
  reconstitution time,
  appearance/clarity,
  pH after reconstitution.

RP-HPLC was run to confirm processing didn't influence purity of Vancomycin.

Lyophilization Cycle

The product was freeze-dried according the following nominal lyophilization cycle parameters:

| Step No | Description | Temperature (° C.) | Pressure | Time (hh:mm) |
|---|---|---|---|---|
| 1 | Load | 20 | Atmospheric | NA |
| 2 | Product freezing | 20→−45 | Atmospheric | 01:05 |
| 3 | Freeze soak time | −45 | Atmospheric | 02:00 |
| 4 | Evacuation | −45 | 200 μbar | 00:01 |
| 5 | Primary drying | −45→ 0 | 200 μbar | 04:00 |
| 6 | Primary drying | 0 | 200 μbar | 02:00 |
|   | Primary drying | 0→ 15 | 200 μbar | 02:00 |
|   | Primary drying | 15 | 200 μbar | 24:00 |
| 7 | Secondary drying | 15 → 30 | 200 μbar | 00:15 |
| 8 | Secondary drying | 30 | 200 μbar | 15:00 |
| 9 | Preaeration | | 0.95 bar | NA |
| 10 | Stoppering | | 0.95 bar | NA |
| 11 | Aeration | | Atmospheric | NA |
| | Total length (without stoppering) | | | 50:21 |

Results

An overall average moisture content value of 1.04 wt % was found by Karl Fisher titration.

Cakes had a very cohesive structure even if some cracks were present.

Analytical Results

In Process Controls

| Process step | Analytical Test | Results |
|---|---|---|
| Formulated Bulk solution | pH | 3.69 |
| | Density (g/mL) | 1.0384 |
| | Concentration (UV) | 116.88 mg/mL |

Tests on Freeze-Dried Drug-Product

| Process step | Analytical Test | Results |
|---|---|---|
| Final Lyophilizate | Water content by K F | 1.04% w/w |
| | Visual aspect of the cake | Whitish solid compact mass |
| | Reconstitution time | 30 seconds |
| | Appearance of reconstituted solution (water, 50 mg/ml) | Clear, colourless solution |
| | pH | 3.44 |
| | % Vancomycin B by RP-HPLC | 93.3% |

Moisture Content (K.F.)

| Sample | Moisture |
|---|---|
| Sample 1 (back) | 1.07% |
| Sample 2 (middle) | 1.02% |
| Sample 3 (front) | 1.02% |
| Overall average | 1.04% |

HPLC Assay (% Vancomycin B)

| Sample | Vancomycin B |
|---|---|
| Sample 1 (back) | 93.3% |
| Sample 2 (middle) | 93.3% |
| Sample 3 (front) | 93.3% |
| Overall average | 93.3% | pH

| Sample | pH |
|---|---|
| Sample 1 (back) | 3.45 |
| Sample 2 (middle) | 3.44 |
| Sample 3 (front) | 3.44 |
| Overall average | 3.44 |

Reconstitution Time

About 30 seconds were needed to completely reconstitute the freeze-dried drug product with 5.0 mL of WFI. The reconstituted solution had a clear, colorless appearance and was particle free.

Example 4

Summary

Nebulization characteristics of gentamicin and vancomycin solutions were evaluated as a function of solution strength, nebulizer fill volume, and saline concentration. Key aerosol attributes measured were emitted dose and particle size distributions. All experiments were performed using Aerotech II jet nebulizers operated continuously at 8 LPM. For gentamicin solutions in WFI, the range of solution strengths varied from 40 to 120 mg/ml, and fill volumes ranged from 2 to 4 ml. The resulting aerosol dose emitted over 30 minutes of nebulization was found to vary from 40 mg to over 300 mg, with the dose increasing proportionally with increasing fill volume and solution strength. Emitted dose measurements for vancomycin were performed for solutions in normal saline, in 0-45% saline, and in water for injection, lire range of solution concentrations tested ranged from 60 mg/ml to 140 mg/ml. The cumulative aerosol dose emitted for a 30 minute nebulization period varied from about 50 mg to over 300 mg, with the dose increasing proportionally with solution strength and fill mass.

Particle size distributions were measured for the above drug solutions using a laser diffraction spectrometer. The median particle size for all solutions tested was in the range 2-3 μm, well within the respirable size range. Particle size distributions for these antibiotic drugs were found to be relatively insensitive to solution strength and fill volume. Follow-on measurements with drug and normal saline solutions indicated that the size distribution of nebulized antibiotics were comparable to that for the normal saline solution.

Combined together, the above results indicate that a broad range of aerosol doses in the respirable range may be achieved for nebulized vancomycin and gentamicin by suitably selecting nebulizer fill volume and solution strengths.

Objectives

To determine the amount of drug aerosol emitted during the nebulization of gentamicin and vancomycin solutions, as a function of nebulizer fill volume and solution strength.

To determine the size distribution of aerosols produced during the nebulization of gentamicin, vancomycin, and saline solutions as a function of nebulizer fill volume and solution strength.

Introduction

This Example involves assessing nebulization characteristics such as the emitted dose and droplet size distribution for antibiotic drug solutions of different strengths and at different nebulizer fill volumes. The emitted dose information is useful in selecting solution strengths and fill masses to deliver a chosen target dose. The particle size information is useful in determining whether the aerodynamic size of the aerosol produced is in the range required for effective lung deposition (1-5 μm). Results for a placebo solution (i.e., normal saline) are also reported for comparison. All of the experiments were performed using an Aerotech II jet nebulizer operated continuously at a nominal flow rate of 8 LPM Aerosol emitted dose was estimated by using filters to collect the aerosol output generated by the nebulizer, and assaying the amount, of drug deposited. Particle size distributions of the generated aerosol were measured using a Sympatec laser diffraction spectrometer.

Study Design

Characterization of Emitted Dose

For the case of gentamicin solution in water, a full factorial experiment was performed to characterize emitted mass of aerosol as a function of two factors, i.e. nebulizer fill volume and fill mass. The range of solution strengths and fill volume was chosen to provide a broad range of target doses achievable with a nebulization time of 30 minutes.

The test matrix for this experiment is presented in Table 1. Gentamicin solution strength (based on mass of drug) was varied from 40 mg/ml to 120 mg/ml, while the nebulizer fill volume was varied from 2 to 4 ml. Bach of the 9 treatment combination was repeated twice, for a total of 18 runs. The gentamicin solutions were prepared in water for injection (WFI), and were preservative free.

For the case of vancomycin, the emitted mass of aerosol was characterized for following three cases:

Vancomycin in normal saline, solution strength of 60 mg/ml, nebulizer fill volume ranging from 2-4 mL Vancomycin in 0.45% saline, solution strength ranging from 60-90 mg/ml, nebulizer fill volume ranging from 2-4 ml.

Vancomycin in WFI, solution strength ranging from 60-140 mg/ml, nebulizer fill volume ranging from 2-4 ml.

In the case of vancomycin, addition of salt to the formulation allows for tuning of solution properties such as osmolality. Test matrices for the above three experiments are presented in Tables 2-4.

TABLE 1

Test Matrix for Gentamicin Solution in WFI

| Pattern | Fill Volume [ml] | Solution Strength [mg/mL] |
|---------|------------------|---------------------------|
| 13 | 2 | 120 |
| 31 | 4 | 40 |
| 22 | 3 | 80 |
| 12 | 2 | 80 |
| 11 | 2 | 40 |
| 21 | 3 | 40 |
| 21 | 3 | 40 |
| 13 | 2 | 120 |
| 23 | 3 | 120 |
| 31 | 4 | 40 |
| 33 | 4 | 120 |
| 11 | 2 | 40 |
| 22 | 3 | 80 |
| 12 | 2 | 80 |
| 23 | 3 | 120 |
| 33 | 4 | 120 |
| 32 | 4 | 80 |
| 32 | 4 | 80 |

TABLE 2

Test Matrix for Vancomycin Solution (60 mg/ml) in Normal Saline
Vancomycin at 60 mg/ml (in normal saline)

| | |
|---|---|
| Fill volume | 2 ml |
| Fill volume | 3 ml |
| Fill volume | 2 ml |
| Fill volume | 4 ml |
| Fill volume | 4 ml |
| Fill volume | 3 ml |
| Fill volume | 3 ml |
| Fill volume | 4 ml |
| Fill volume | 2 ml |

The responses measured for all of the above experiments included:

(i) the mass of drug delivered in 15 mins (ii) the cumulative mass of drug delivered in 30 mins, and (iii) the mass of drug remaining in the nebulizer after 30 mins of operation.

TABLE 3

Test Matrix for Vancomycin Solution in 0.45% Saline

| Pattern | Fill Volume [ml] | Solution Strength [mg/L] |
|---|---|---|
| 11 | 2 | 60 |
| 13 | 2 | 90 |
| 13 | 2 | 90 |
| 11 | 2 | 60 |
| 32 | 4 | 75 |
| 23 | 3 | 90 |
| 12 | 2 | 75 |
| 21 | 3 | 60 |
| 23 | 3 | 90 |
| 32 | 4 | 75 |
| 21 | 3 | 60 |
| 33 | 4 | 90 |
| 12 | 2 | 75 |
| 33 | 4 | 90 |
| 22 | 3 | 75 |
| 31 | 4 | 60 |
| 31 | 4 | 60 |
| 22 | 3 | 75 |

TABLE 4

Test Matrix for Vancomycin Solution in WFI

| Pattern | Fill Volume [ml] | Solution Strength [mg/ml] |
|---|---|---|
| 11 | 2 | 60 |
| 13 | 2 | 140 |
| 13 | 2 | 140 |
| 11 | 2 | 60 |
| 32 | 4 | 100 |
| 23 | 3 | 140 |
| 12 | 2 | 100 |
| 21 | 3 | 60 |
| 23 | 3 | 140 |
| 32 | 4 | 100 |
| 21 | 3 | 60 |
| 33 | 4 | 140 |
| 12 | 2 | 100 |
| 33 | 4 | 140 |
| 22 | 3 | 100 |
| 31 | 4 | 60 |
| 31 | 4 | 60 |
| 22 | 3 | 100 |

Characterization of Particle Size Distribution

For the case of gentamicin solution in water, a full factorial experiment experiment was performed to characterize the particle size distribution of aerosol as a function of two factors, i.e. nebulizer fill volume and fill mass. The test matrix for this experiment is presented in Table 5. Gentamicin solution strength (based on mass of drug) was varied from 40 mg/ml to 120 mg/ml, while the nebulizer fill volume was varied from 2 to 4 ml. The 9 treatment combinations were run in a random order. A fresh nebulizer was used for each run. The nebulizers in this experiment were prequalified using a flow rate test to minimize variability in the test results.

TABLE 5

Test Matrix for Gentamicin Solution in WFI

| Run | Pattern | Fill Volume [mL] | Solution Strength [mg/mL] |
|---|---|---|---|
| 1 | 31 | 4 | 40 |
| 2 | 32 | 4 | 80 |
| 3 | 21 | 3 | 40 |
| 4 | 23 | 3 | 120 |
| 5 | 22 | 3 | 80 |
| 6 | 13 | 2 | 120 |
| 7 | 11 | 2 | 40 |
| 8 | 33 | 4 | 120 |
| 9 | 12 | 2 | 80 |

For the case of vancomycin, the emitted mass of aerosol was characterized for following three cases:

Vancomycin in normal saline, solution strength of 60 mg/ml, nebulizer fill volume ranging from 2-4 ml.

Vancomycin in 0.45% saline, solution strength ranging from 60-90 mg/ml, nebulizer fill volume ranging from 2-4 ml.

Vancomycin in WFI, solution strength ranging from 60-140 mg/ml, nebulizer fill volume ranging from 2-4 ml.

The test matrices for the above three experiments are presented in Tables 6-8. A fresh nebulizer was used for each run. The nebulizers in these experiments were pre-screened using a flow rate test to minimize variability in the test results.

TABLE 6

Test Matrix for Vancomycin Solution (60 mg/ml) in Normal Saline

| Run | Pattern | Fill Volume [mL] | Solution Strength [mg/mL] |
|---|---|---|---|
| 1 | 1 | 2 | 60 |
| 2 | 3 | 4 | 60 |
| 3 | 2 | 3 | 60 |

TABLE 7

Test Matrix for Vancomycin Solution in 0.45% Saline

| Run | Pattern | Fill Volume [mL] | Solution Strength [mg/mL] |
|---|---|---|---|
| 1 | 12 | 2 | 75 |
| 2 | 31 | 4 | 60 |
| 3 | 22 | 3 | 75 |
| 4 | 33 | 4 | 90 |
| 5 | 13 | 2 | 90 |
| 6 | 11 | 2 | 60 |
| 7 | 32 | 4 | 75 |
| 8 | 21 | 3 | 60 |
| 9 | 23 | 3 | 90 |

TABLE 8

Test Matrix for Vancomycin Solution in WFI

| Run | Pattern | Fill Volume [mL] | Solution Strength [mg/mL] |
|---|---|---|---|
| 1 | 33 | 4 | 140 |
| 2 | 22 | 3 | 100 |
| 3 | 13 | 2 | 140 |
| 4 | 12 | 2 | 100 |

TABLE 8-continued

Test Matrix for Vancomycin Solution in WFI

| Run | Pattern | Fill Volume [mL] | Solution Strength [mg/mL] |
|---|---|---|---|
| 5 | 11 | 2 | 60 |
| 6 | 32 | 4 | 100 |
| 7 | 21 | 3 | 60 |
| 8 | 23 | 3 | 140 |
| 9 | 31 | 4 | 60 |

A follow on experiment was performed to characterize particle size distributions of aerosols generated using vancomycin and gentamicin solutions in water at a fixed solution strength of 120 mg/ml, and a fixed fill volume of 5 ml. Particle size distributions of drug aerosol were compared against those obtained by nebulizing normal saline solution at a fill volume of 5 ml. The test matrix for this follow on experiment is presented in Table 9. Each treatment was repeated 3 times.

TABLE 9

Test Matrix for Evaluation of Drug and Placebo Solutions

| Run | Drug | Fill Volume [mL] |
|---|---|---|
| 1 | Normal Saline | 5 |
| 2 | Vancomycin | 5 |
| 3 | Gentamicin | 5 |
| 4 | Gentamicin | 5 |
| 5 | Normal Saline | 5 |
| 6 | Gentamicin | 5 |
| 7 | Vancomycin | 5 |
| 8 | Vancomycin | 5 |
| 9 | Normal Saline | 5 |

Equipment And Materials
Equipment
Sympatec HELOS Magic BFS laser diffraction spectrometer, Ser. No. 085
Mass flow meter (TS14000 series)
Rotameter
Volumetric flow meter, Dry Cal
Pressure regulator
Flow regulating valve
Flow shut-off valve
Pipet
Materials
Aerotech II Nebulizer
Tee connector and mouthpiece from Hudson RCI Micro-Mist Nebulizer (Cat No. 1882)
Inspiratory filter (PARI electret filter)
Filter holder
One way valve
50 ml centrifuge tubes
HPLC water
HPLC water dispenser
Vancomycin HCl
Gentamycin Sulfate
Procedure
Characterization of Emitted Dose
The nebulizer was connected to a standard "T" piece coupled to a filter holder on one end, and a flow inlet channel provided with a one-way valve on the other end. The filter holder supported a PARI electret filter used to collect the aerosol dose emitted by the nebulizer.

The nebulizer was operated using clean, dry compressed air from a source regulated to a pressure of about 50 psig. The flow rate of air through the nebulizer was controlled using a rotometer and set to a nominal flow rate 8 LPM. The drug laden air from the nebulizer passed through the collection filter into an exhaust line provided with a backup filter and a flow regulating valve, and connected to a vacuum source. The flow regulating valve was set so that the vacuum suction flow was slightly higher than the nebulizer output flow. A small amount of clean make up air was allowed to enter through the one way valve to make up for the flow deficit. This arrangement enabled efficient collection of the nebulizer drug output by the filter. The emitted dose experiments ware performed with the nebulizer operating continuously at 8 LPM for a total nebulization time of 30 minutes. The filter/filter holder were replaced with a fresh filter/filter holder at the 15 minute point, so that the accumulated drug output at 15 minutes and 30 minutes could be evaluated. The filter samples were placed in centrifuge tubes and rinsed with a pre-determined amount of HPLC water (ranging from 30-40 ml). Residual drug from each filter holder was also rinsed into the corresponding centrifuge tube using some of the filter rinsate. The residual drug from the nebulizer was also rinsed into a 50 ml centrifuge tube using a pre-determined amount of HPLC water (ranging from 30-40 ml). The drug content of the filler and nebulizer samples were assessed by drug specific HPLC assays. Note that the measurement of filter and nebulizer samples permit a full mass balance to be performed for each run.

Characterization of Particle Size Distribution

Droplet size distributions for aerosolized drug and placebo solutions were measured using the Sympatec HELOS laser diffraction spectrometer. In preparation for a run, the nebulizer was connected to the compressed air line, the flow turned on and the pressure regulator set to a driving pressure to generate a flow rate of 8 LPM through the nebulizer. The flow was then turned off by closing the flow shut-off valve. Next, the nebulizer was connected to a "T" piece with one port plugged, and the other port coupled to a mouthpiece. The nebulizer was then filled with drug solution, and mounted so that nebulizer mouthpiece was aligned parallel to the nozzle of the Rodos dry powder disperser apparatus already installed in the spectrometer. The laser diffraction system was setup to automatically trigger when it sensed the presence of the aerosol generated by the nebulizer. Measurements were initiated by opening the shut-off valve to pressurize the nebulizer and generate the aerosol. A total of 6 particle size distribution scans were taken for each nebulizer run, and then averaged to provide representative size distribution results.

Results and Discussion
Characterization of Emitted Dose

Figure 4B:
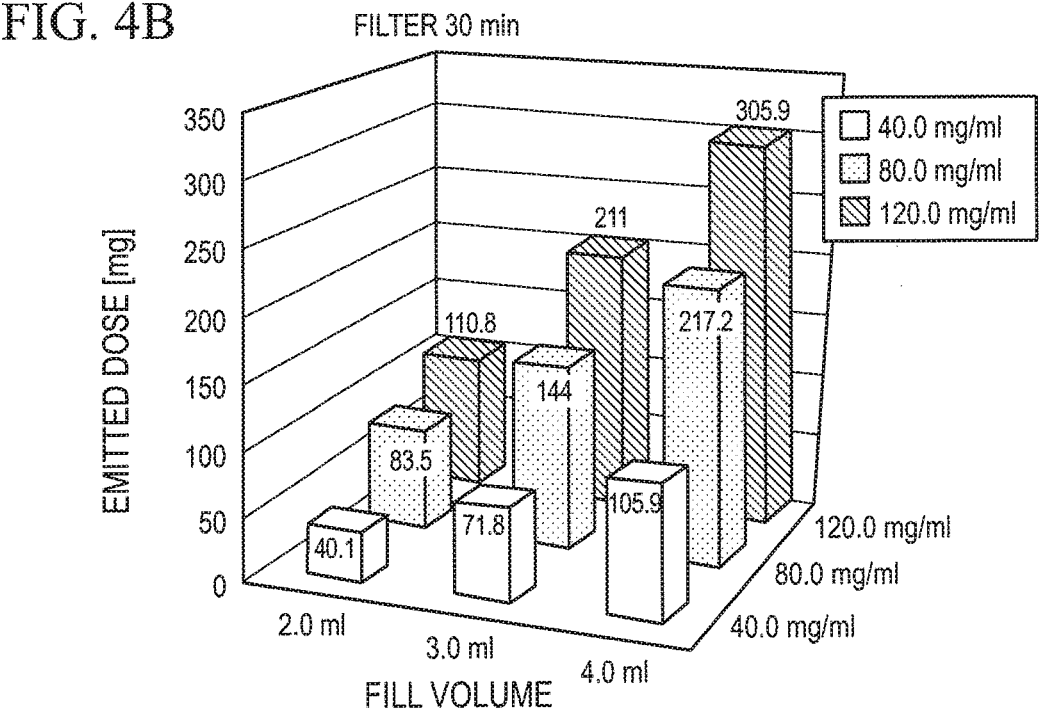
Figure 5:
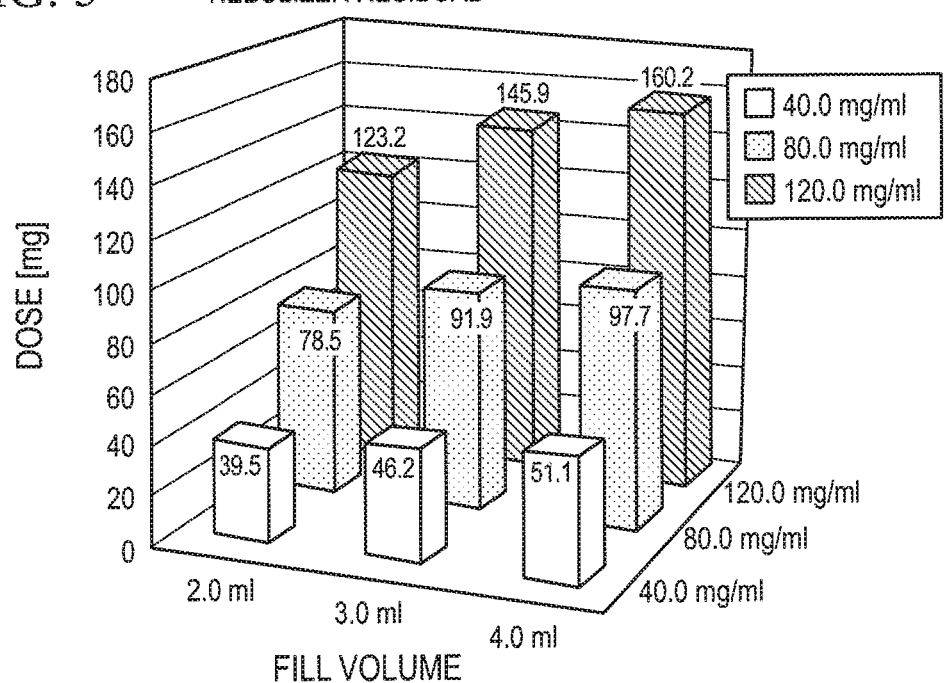
FIG. 5 shows gentamicin residual dose retained in a nebulizer as a function of fill volume and solution strength.

Summarized dose delivery results for the case of gentamicin solutions are presented in FIGS. 3-5. FIG. 3 is a bar graph showing the total drug recovered from the nebulizer and as a function of nebulizer fill volume and solution strength. Each recovery value is the average of two replicate runs (run order listed in Table 1). The drug recovery was very consistent across solution strengths and fill volumes, varying in the range 97.1%-101.2% of fill mass, indicating that a full mass balance was achieved from these measurements.

FIGS. 4a and 4b present the cumulative emitted dose of gentamicin, respectively at the 15 min and 30 min time points, as a function of fill volume and solution strength. Again, each value reported is the average of two replicate runs. The delivered dose was observed to increase with an increase in both fill volume and solution strength, consistent with expectation. A comparison of these two figures shows that the collected dose at 15 minutes was comparable to that at 30 minutes for 2 and 3 ml fill volumes, indicating that the dose emission at these fill volumes occurred within 15 minutes. For the 4 ml fill volume, the collected dose at 30 mins was only slightly larger than the value at 15 minutes, indicating that nebulization was largely completed within the 15 minute period. From this it can be concluded that fill volumes of up to 4 ml of gentamicin solution of strengths up to 120 mg/ml can be effectively nebulized within a duration of 30 minutes. FIG. 4b also indicates that a gentamicin aerosol doses spanning a factor of up to 7 can be delivered from the nebulizer by suitably tuning the solution strength and fill volume within the ranges tested.

FIG. 5 presents the gentamicin dose retained by the nebulizer at the end of 30 minutes, as a function of solution strength and fill volume. The values reported are averages of two replicate runs. The retained dose was found to increase with increasing solution strength and fill volume, with a steeper increase observed with increasing solution strength.

Similar trends in emitted dose as a function of solution strength and fill volume were obtained for the case of vancomycin. Illustrative emitted dose measurements for vancomycin are presented in FIGS. 6-8.

For the case of 60 mg/ml solution in normal saline (see Table 2), FIG. 6 plots the distribution of vancomycin drug after 30 minutes of nebulization as a function of fill volume. The plot shows the dose retained in the nebulizer and that collected at the 15 minute (filter 1) and 30 minute (filter 2) timepoint. The reported values are averages calculated for 3 replicate runs. As with the case of gentamicin, dose emission was found to be largely completed within 15 minutes, and the accumulated dose (i.e. filter 1+filter 2) at the end of 30 minutes was found to increase with fill volume.

Figure 8:
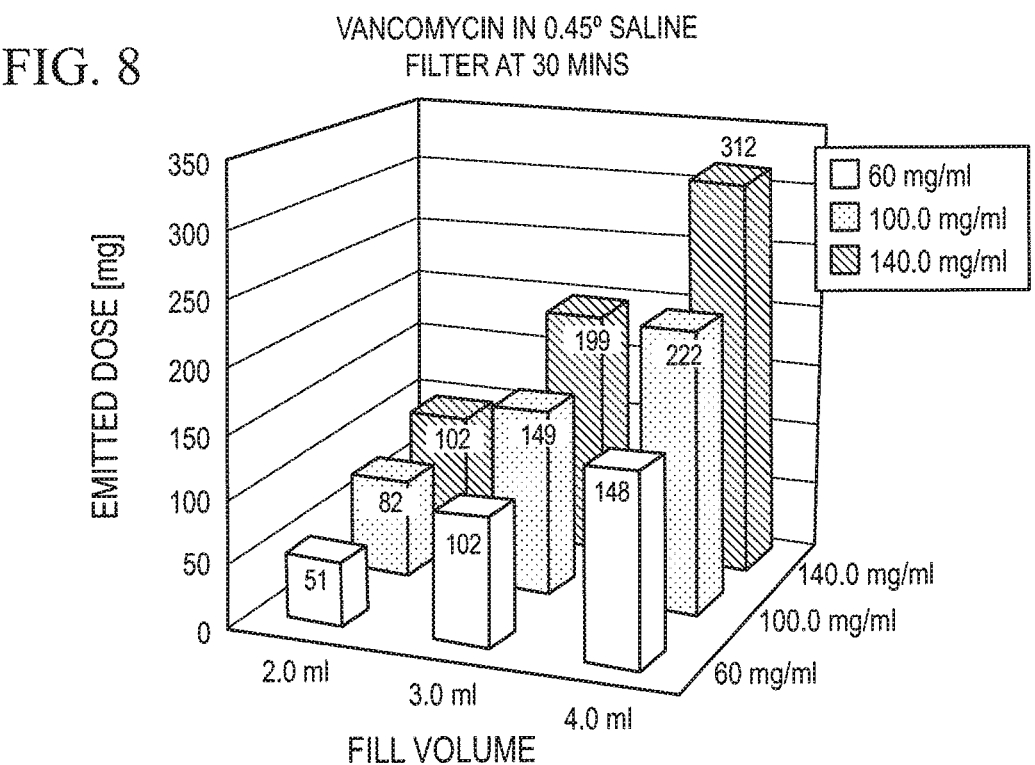
FIG. 8 shows emitted dose as a function of solution strength and fill volume, for the case of vancomycin solution in water for injection (WFI).

For the case of vancomycin solutions in 0.45% saline (see test matrix in Table 3), FIG. 7 plots the cumulative emitted dose after 30 minutes of nebulization as a function of solution strength and fill volume. The delivered dose was observed to increase with increasing fill volume and solution strength, as expected. FIG. 8 plots similar results for the case of vancomycin solutions in WFI, obtained for the test matrix presented in Table 4.

It is clear from FIGS. 6-8 that aerosol doses of vancomycin spanning a six fold range can be obtained from the nebulizer by suitably tuning the fill volume and solution strength within the ranges tested.

Characterization of Particle Size Distribution

Figure 9:
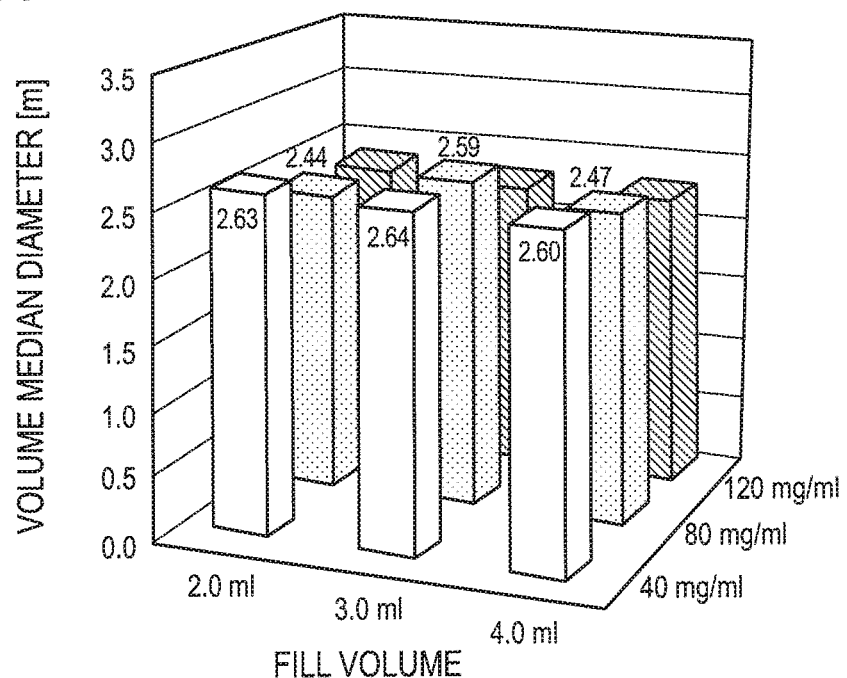
FIG. 9 shows volume median diameter for nebulized gentamicin as a function of solution strength and fill volume.
Figure 10:
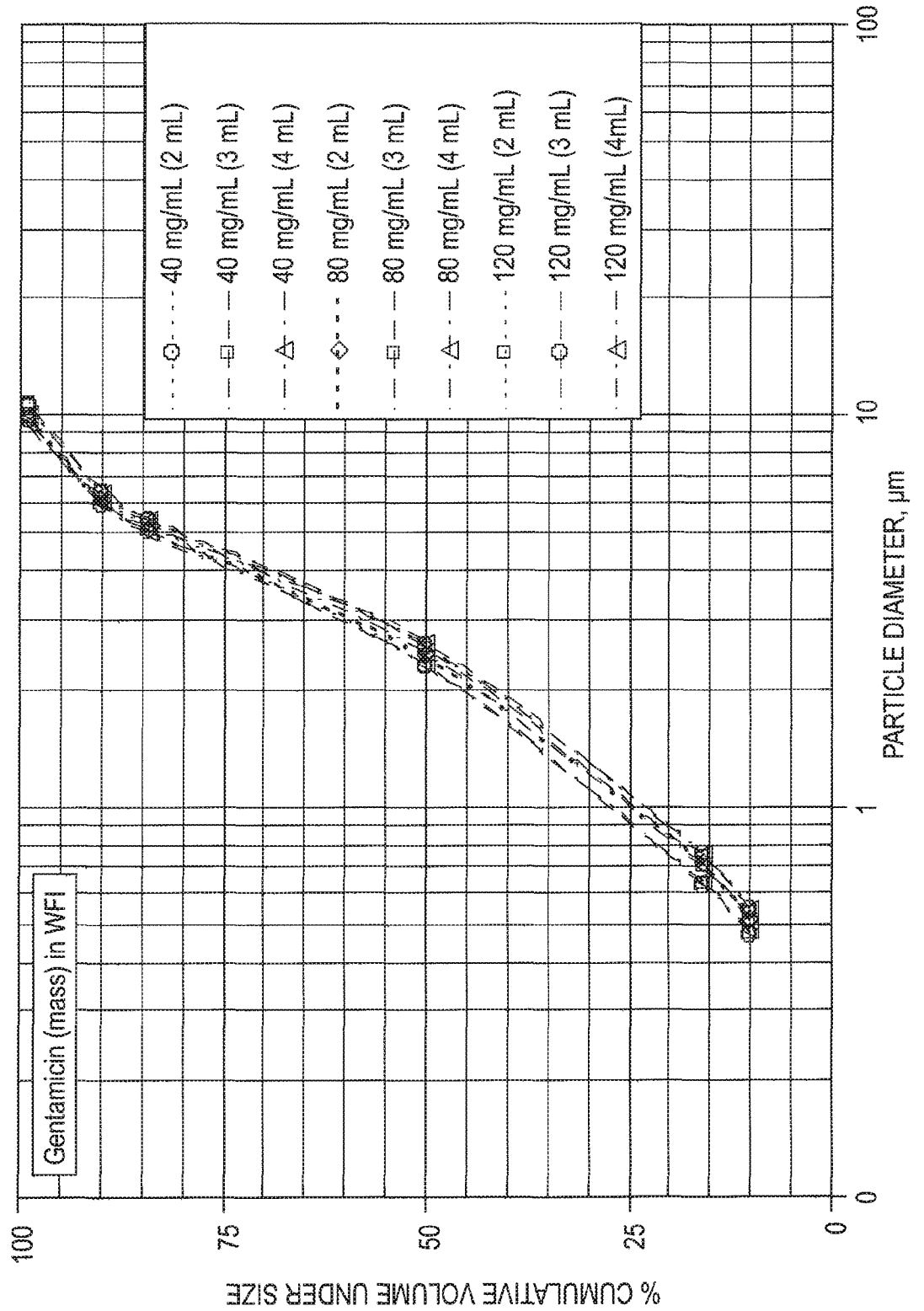
FIG. 10 shows cumulative particle size distributions for gentamicin at different solution strengths and nebulizer fill volumes.

Representative laser diffraction particle size measurements for the case of gentamicin solutions (test matrix of Table 5) are summarized in FIGS. 9 and 10. FIG. 9 plots the volume median diameter for aerosolized gentamicin as a function of fill volume and solution strength (test matrix in Table 5). Each reported value was obtained by averaging 6 replicate laser diffraction measurements for each nebulization run. The measured median particle size for all of the gentamicin solutions varied slightly in the 2-3 μm range, and appeared to be relatively insensitive to fill volume or solution strength. In all cases, the median particle diameter was well within the "respirable size range" considered to be suitable for pulmonary drug delivery (1-5 μm). FIG. 10 plots the cumulative volume weighted particle size distributions for gentamicin aerosol for all of the solution strengths and fill volumes tested. The size distributions obtained for these solutions were observed to vary within a narrow range over the fill volumes and solution strengths tested. FIG. 10 also provides a measure of the spread of the aerosol size distribution, and it was observed that a major fraction of the aerosol was within the respirable size range.

Figure 11:
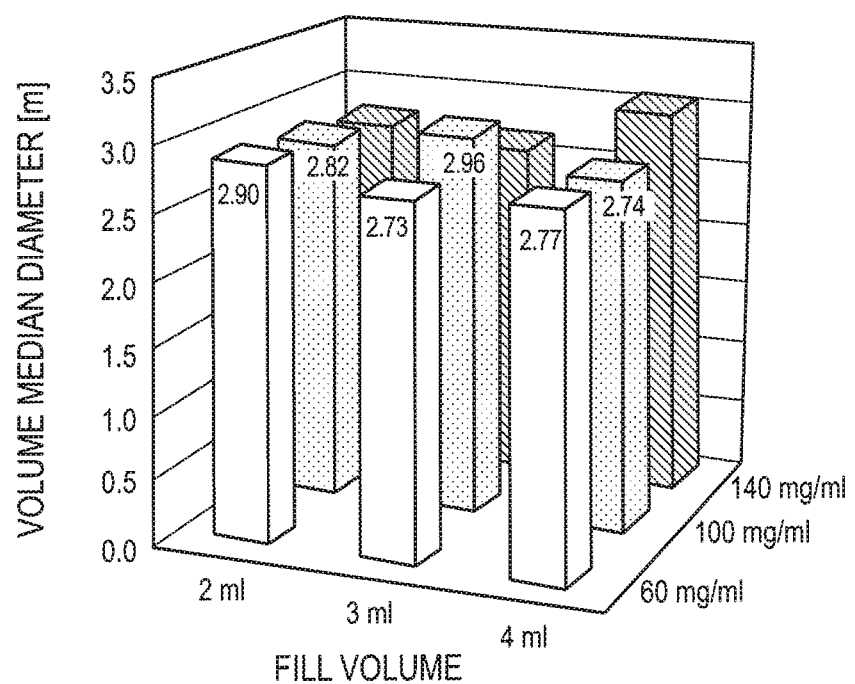
FIG. 11 shows volume median diameter for nebulized vancomycin (solution in WFI) as a function of solution strength and fill volume.
Figure 12:
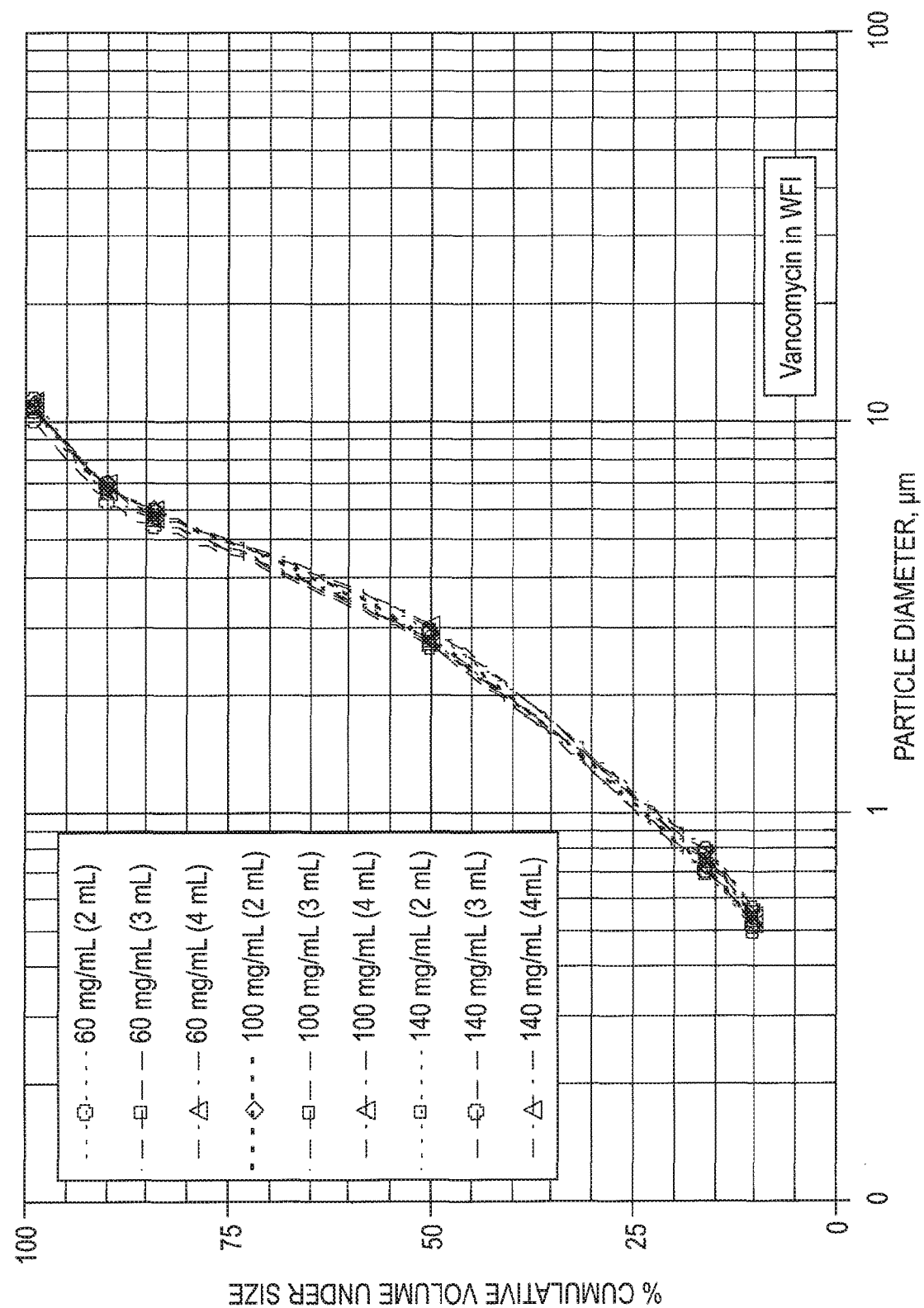
FIG. 12 shows cumulative particle size distributions for nebulized vancomycin (solution in WFI) at different solution strengths and nebulizer fill volumes

Representative particle sizing measurements for vancomycin solutions in WFI (test matrix in Table 8) are presented in FIGS. 11 and 12, and are roughly comparable to that obtained for gentamicin solutions.

FIG. 11 indicates that the volume weighted median sizes for these vancomycin solutions were largely within the range of 2-3 also well within the respirable range. The spreads of the aerosol size distribution, shown in FIG. 12, were similar to that obtained for nebulized gentamicin.

FIGS. 13 and 14 are plots of volume median diameter for the case of vancomycin solutions in normal saline (test matrix in Table 6), and 0.45% saline (test matrix in Table 7) respectively, obtained at different solution strengths and fill volumes. The size distributions were found to be comparable to that obtained for the vancomycin solutions in water. In general, the size distributions of vancomycin solutions were largely insensitive to fill volume, solution strength, and saline concentration.

Finally, results from the follow-on particle sizing study with the test matrix listed in Table 9 are presented in FIG. 15. This figure plots volume median diameters for solutions of vancomycin (120 mg/ml), gentamicin (120 mg/ml) and normal saline, all obtained for nebulizer fill volumes of 5 ml. For each solution, results from three nebulizer runs are provided. It is seen from this plot that the median particle size for all three solutions were comparable and were in the 2-3 μm range, well within the respirable size range.

Conclusions

The emitted dose of nebulized gentamicin and vancomycin was measured as a function of solution strength, fill volume, and saline concentration. All experiments were performed using Aerotech II jet nebulizers operated continuously at 8 LPM. For gentamicin solutions in WFI, the range of solution strengths varied from 40 to 120 mg/ml, and fill volumes ranged from 2 to 4 ml. The resulting aerosol dose emitted over 30 minutes of nebulization was found to vary from 40 mg to over 300 mg, with the dose increasing with increasing fill volume and solution strength. Emitted dose measurements for vancomycin were performed for solutions in normal saline, in 0.45% saline, and in water for injection. The range of solutions tested ranged from 60 mg/ml to 140 mg/ml. The cumulative aerosol dose emitted over a 30 minute nebulization period varied from about 50 mg to over 300 mg, with the dose increasing with solution strength and fill mass.

Particle size distributions were measured for the above drug solutions using a laser diffraction spectrometer. The median particle size for all solutions tested was in the range 2-3 μm, well within the respirable size range. Particle size distributions for these antibiotic drugs were found to be relatively insensitive to solution strength and fill volume. Follow-on measurements with drug and normal saline solutions indicated that the size distribution of nebulized antibiotics were comparable to that for the normal saline solution.

Combined together, the above results demonstrate that a broad range of aerosol doses in the respirable range may be achieved for nebulized vancomycin and gentamicin by suitably selecting nebulizer fill volume and solution strengths.

Example 5

This Example involved evaluating the potential toxicity and recovery resulting from a 14-consecutive day, nose-only inhalation administration of vancomycin hydrochloride (vancomycin) to CD rats.

Within 2 hours prior to usage, a vancomycin nebulizer solution having a concentration of 120 mg/ml (based on vancomycin potency of bulk material) was formed by dissolving vancomycin hydrochloride (available from Alpharma, Copenhagen, Denmark) in sterile water for injection USP (available from B. Braun Medical Inc., Bethlehem, Pa.). The solution was used to generate aerosolized vancomycin for all vancomycin exposure groups.

Nose-only exposures were conducted in a "flow-past" cylindrical inhalation chamber placed inside a steel-framed Plexiglas secondary containment box. The chamber contained 48 animal ports, each compatible with a single nose-only exposure tube, aerosol concentration sampling device (e.g., filter), or oxygen monitor.

The total air flow through the exposure system was balanced to achieve individual animal port flows of ~500 mL/min (port flow approximated based on total chamber flow). Measured flows included sample flow rate, nebulizer flow rate, dilution flow rate (chamber make-up air), and chamber exhaust flow. The exposure chamber had a slightly higher exhaust flow rate than inlet flow rate.

Vancomycin solution was aerosolized with two Aerotech II nebulizers operated at 20 psi driving pressure. The target aerosol Vancomycin concentration for all exposure levels was ~1.0 mg/L.

Aerosolized vancomycin was administered to 3 groups of male and female CD rats (available from Charles River Laboratories, Kingston, N.Y.) for durations of 30 min (Low), 90 min (Mid), and 180 min (High). A control group was exposed for 180 min to aerosols generated from a normal saline solution. Groups of rats from the Control and High level 14-day exposures were also studied following a 14-day recovery period. Endpoints included clinical observations, body weights, clinical pathology (hematology, clinical chemistry), urinalyses, organ weights, and histopathology.

Vancomycin aerosol concentrations were 1.23±0.16, 1.25±0.12, and 1.23±0.08 mg/L for the Low, Mid, and High exposure levels, respectively. Mean particle size was determined to be in the inhalable size range for rodents (2.0-2.6 μm mass median aerodynamic diameter). Mean total inhaled doses were estimated as 23, 71 and 139 mg/kg, and mean doses deposited in lung were estimated as 3, 9, and 17 mg/kg for the Low. Mid, and High exposure levels, respectively.

The vancomycin exposures were well-tolerated by all groups of rats. All rats survived to scheduled necropsy, and there were no vancomycin related effects noted on clinical observations. There were also no vancomycin treatment related effects on body weight.

The only organ weights to show consistent vancomycin related effects were lungs. Lung weights were statistically significantly increased by an average approximately 8, 20, 19% of control for the Low, Mid and High exposure levels respectively.

Exposure related histopathologic findings were limited to the respiratory tract. Observations included minimal to mild nasal mucous cell hyperplasia and hypertrophy, minimal to mild pulmonary interstitial inflammation and alveolar macrophage hyperplasia with an apparent dose-response effect, lymphoid hyperplasia of the tracheobronchial and mediastinal lymph nodes, and slight laryngeal inflammation. There was substantial diminution of these findings after 14 days of recovery with pulmonary interstitial inflammation, alveolar macrophage hyperplasia, and nasal mucus cell hyperplasia persisting in the high dose group, but at a lesser severity overall than seen at the end of exposure. A threshold of response was not established although the effects in the low dose group were generally minimal.

Clinical pathology findings were generally unremarkable. The only vancomycin related effect on hematology was a statistically significant increase in neutrophils at the Mid and High exposure levels. The only vancomycin related effect on clinical chemistry was a mild but statistically significant increase in aspartate aminotransferase (AST) values (~28-46%) at the Mid and High exposure levels. Neutrophil changes were diminished after the recovery period resolved. AST observations resolved after the recovery period. Both findings likely resulted from the minimal to mild pulmonary inflammation manifested in the histopathology findings. No vancomycin related changes were seen after examination of serum indicators of kidney function or urinalysis.

To conclude, the findings indicate that exposure to vancomycin at the Mid level and High level exposures, predominantly, caused an irritant reaction in the respiratory tract manifested by minimal to moderate mucous cell changes in the nose and minimal to mild inflammation and macrophage hyperplasia in the lungs. Corresponding changes in neutrophil and AST values likely resulted from the pulmonary inflammatory findings. Recovery from these effects was evident, but not entirely resolved after the 14-day observation period. A no observed effect level was not established.

Example 6

This Example involved evaluating the potential toxicity and recovery resulting from a 14-consecutive day, face mask inhalation administration of vancomycin hydrochloride to beagle dogs.

Within 2 hours prior to usage, a vancomycin nebulizer solution having a concentration of 120 mg/ml was formed by dissolving vancomycin hydrochloride (available from Alpharma, Copenhagen, Denmark) in sterile water for injection USP (available from B. Braun Medical Inc., Bethlehem, Pa.). The solution was used to generate aerosolized vancomycin for all vancomycin exposure groups.

The exposure system consisted of a single, cylindrical, plexiglass inhalation chamber (volume of ~23.7 L, 14.61-cm radius, 35.56-cm height). The chamber was supplied with two Aerotech II nebulizers operated at ~40 psi. Nebulized test article and nebulizer air supply was diluted with ~10 L/min HEPA-filtered dilution air. The flow through the system was ~36 L/min.

The aerosolized vancomycin was administered via a face mask to 3 groups of male and female beagle dogs for durations of 15 min (Low), 30 min (Mid), and 60 min (High). A control group was exposed for 60 min to aerosols generated from normal saline solution, i.e., 0.9% sodium chloride injection USP (available from B. Braun Medical Inc.).

Groups of dogs from the (Control and High level 14-day exposures were also studied following a 14-day recovery period. Endpoints for all groups of dogs included physical examinations, clinical observations, body weights, ophthalmology, cardiovascular EKG, clinical pathology (hematology, clinical chemistry), urinalyses, organ weights, histopathology, and toxicokinetics.

Vancomycin aerosol concentrations were 1.39±0.20, 1.51±0.19, and 1.49±0.15 mg/L for the Low, Mid, and High exposure levels, respectively. Mean particle size was determined to be in the inhalable size range for dogs (1.9-2.6 μm mass median aerodynamic diameter). Mean total inhaled doses were estimated as 10, 23, and 45 mg/kg, and mean doses deposited in lung were estimated as 2, 5, and 9 mg/kg for the Low, Mid, and High exposure levels, respectively.

The vancomycin exposures were well-tolerated by all groups of dogs. All dogs survived to scheduled necropsy. There were no vancomycin related effects noted on physical examinations, clinical observations, ophthalmology, cardiac ECG tracings, hematology, clinical chemistry, urinalyses, gross necropsy observations, and organ weights.

Histopathology examinations of tissues revealed no effect of Vancomycin exposure in the organs and tissues examined outside of the respiratory tract. Likewise, there was an absence of microscopic alterations in the nasal cavity/turbinates, larynx, and trachea. The effects of Vancomycin exposure were limited to microscopic findings in the lung. Treatment-related increased incidence of minimal to mild chronic interstitial inflammation, alveolar histiocytosis, and bronchial lymph node lymphoreticular hyperplasia were observed. Among Control and High level animals in the Recovery groups there were no treatment-related differences in the macroscopic and microscopic findings.

In conclusion, effects of Vancomycin exposure were limited to minimal to mild pulmonary histopathology at the termination of exposure. Recovery of histopathological effects was complete after 14 days. The minimal to mild chronic interstitial inflammation was generally comparable with background inflammatory changes in beagle dogs. The alveolar histiocytosis was reflective of enhanced clearance that occurs without alveolar injury. The lymphoreticular hyperplasia was considered an adaptive response that facilitates lung clearance mechanisms. Since corresponding fibrosis and alveolar epithelial injury were not characteristic of the observed effects, the lung changes and related lymph node changes were not considered adverse effects. Based on these findings, the no observed adverse effect level (NOAEL) was the high exposure level corresponding to an inhaled dose of 45 mg/kg and a deposited lung dose of 9 mg/kg.

Example 7

Amikacin Sulfate sterile solution for inhalation, 125 mg/ml was manufactured and characterized as follows. Approximately 13.5 L of sterile water for injection was added to a glass carboy fitted with a lightning labmaster mixer. Amikacin sulfate was added to the carboy and the solution was stirred. The solution was mixed until the entire API was dissolved. A sample of the solution was taken and pH measured. With continued stirring, pH was adjusted with 1.0N HCl to be within 5.5-6.3 with a target pH of 5.9. After pH adjustment, sufficient quantity of sterile water for injection was added until the final weight of solution of 21.328 g, was reached. The pH of the final solution was verified to be within an acceptable range. The solution was then sparged with filtered nitrogen at a rate of 1.5 L/min for 15 minutes. The solution was then filtered through the 0.22 micron sterile filter.

Prior to filling the solution, each vial was purged with nitrogen. The solution was filled by weight using a Cazzoli filler/stopper machine into 5 ml amber vials to a target, weight of 4.27±0.08 g. The vials were stoppered with 20 mm Teflon-coated stoppers and secured with aluminum flip off seals. Filled vials were stored at 2-8° C. The composition is summarized in Table A below.

TABLE A

| Ingredient | g per batch |
| --- | --- |
| Amikacin Sulfate | 3525.0 g |
| Hydrochloric Acid | qs to pH 5.9 |
| NaOH | qs to pH 5.9 |
| Sterile Water for Injection | qs to 21, 328 g |
| Nitrogen, NF | Qs |

Stability overtime was assessed for as formulation made substantially as show in table A, with regard to total amikacin active, related substances, such as degradation products, appearance, pH, particulates and sterility. Thus samples were stored at 5° C. (Table B), at 25° C./60% relative humidity (RH) (Table Q, and at 40° C./75% RH (Table D). In each case samples were stored in 5 mL amber glass vials, with 20 mm Teflon stoppers and 20 mm aluminum overseals. Results of each of these storage conditions are shown in Tables B, C and D, respectively.

TABLE B

| Attributes | Specification | Initial | 1 mo. | 3 mos. | 6 mos. | 9 mos. | 12 mos. | 18 mos. |
| --- | --- | --- | --- | --- | --- | --- | --- | --- |
|  | 90.0%-110.0% l.s. | 99.8 | 104.6 | 104.0 | 104.3 | 104.9 | 100.0 | 105.5 |
|  |  | 99.8 |  |  |  |  | 100.6 |  |
| Appearance | Meets Test[1] | MT | MT | MT | MT | MT | MT | MT |
| Kanamycin @ rrt 0.72 | Report results | 0.73<br>0.64 | 0.78 | 0.68 | 0.34 | 0.33 | 0.28 | 0.22 |
| Rel. Substance A @ rrt 0.86 | Report results | 0.66<br>0.60 | 0.70 | 0.19 | 0.55 | 0.46 | 0.50 | 0.36 |
| Unidentified @ rrt 0.61 | Report results | 6.90<br>6.27 | 6.81 | 5.38 | 3.38 | 3.02 | 2.90 | 2.29 |
| Unidentified @ rrt 0.67 | Report results | 0.53<br>0.50 | 0.45 | 0.45 | 0.23 | 0.26 | 0.21 | 0.23 |
| Total Related Substances | 10.0% | 8.82<br>8.01 | 8.74 | 6.70 | 4.50 | 4.07 | 3.89 | 3.10 |
| pH | 5.5-6.3 | 5.6 | 5.6 | 5.5 | 5.6 | 5.5 | 5.7 | 5.6 |
| Particulate Matter | Particles = 10 μm NMT 6000 | 50 | 3 | 7 | 24 | 38 | 5 | 2 |
|  | Particles = 25 μm NMT 600 | 0 | 0 | 0 | 0 | 1 | 0 | 0 |
| Sterility | Meets USP | Conforms | NP | NP | NP | NP | MT | NP |

TABLE C

| Attributes | Specifications | Initial | 1 mo. | 3 mos. | 6 mos. |
|---|---|---|---|---|---|
| Assay | 90.0%-110.0% l.s. | 99.8 99.8 | 104.0 | 105.3 | 101.1 |
| Appearance | Meets Test[1] | MT | MT | MT | MT |
| Kanamycin @ rrt 0.72 | Report results | 0.73 0.64 | 0.81 | 0.71 | 0.44 |
| Rel. Substance A @ rrt 0.86 | Report results | 0.66 0.60 | 0.72 | 0.18 | 0.59 |
| Unidentified @ rrt 0.61 | Report results | 6.90 6.27 | 6.87 | 5.28 | 3.55 |
| Unidentified @ rrt 0.67 | Report results | 0.53 0.50 | 0.50 | 0.49 | 0.28 |
| Total Related Substances | 10.0% | 8.82 8.01 | 8.90 | 6.66 | 4.86 |
| pH | 5.5-6.3 | 5.6 | 5.6 | 5.6 | 5.6 |
| Particulate Matter | Particles = 10 μm NMT 6000 | 50 | 12 | 18 | 33 |
|  | Particles = 25 μm NMT 600 | 0 | 1 | 0 | 1 |
| Sterility | Meets USP | Conforms | NP | NP | NP |

TABLE D

| Attributes | Specifications | Initial | 1 mo. | 3 mos. | 6 mos. |
|---|---|---|---|---|---|
| Assay | 90.0%-110.0% l.s. | 99.8 99.8 | 104.1 | 104.7 | 106.3 |
| Appearance | Meets Test[1] | MT | MT | MT | clear, faint yellow solution |
| Kanamycin @ rrt 0.72 | Report results | 0.73 0.64 | 0.99 | 1.06 | 1.00 |
| Rel. Substance A @ rrt 0.86 | Report results | 0.66 0.60 | 0.71 | 0.16 | 0.60 |
| Unidentified @ rrt 0.61 | Report results | 6.90 6.27 | 6.81 | 4.64 | 3.52 |
| Unidentified @ rrt 0.67 | Report results | 0.53 0.50 | 0.54 | 0.60 | 0.61 |
| Total Related Substances | 10.0% | 8.82 8.01 | 9.05 | 6.46 | 5.73 |
| pH | 5.5-6.3 | 5.6 | 5.6 | 5.5 | 5.5 |
| Particulate Matter | Particles = 10 μm NMT 6000 | 50 | 32 | 20 | 27 |
|  | Particles = 25 μm NMT 600 | 0 | 1 | 0 | 1 |
| Sterility | Meets USP | Conforms | NP | NP | NP |

FIG. 16 is a graphical representation of certain of the stability data provided in Tables B, C and D. In the Fig., the line marked by diamonds represents the 5° C. storage condition, the line marked by the squares represents 25° C./60% RH storage conditions and the line marked by the triangle represents 40° C./75% RH storage conditions. The FIG. shows that the percentage related substances, i.e. impurities, diminishes over storage time. It is thought that this is a function of detactability of the impurities. It is evident, however, that the compositions remain stable, with respect to impurities, over time.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of producing a unit dose of an aqueous amikacin composition comprising:
   a) preparing an amikacin solution by dissolving amikacin sulfate in preservative-free water by stirring;
   b) adjusting the pH of the amikacin solution, if necessary, until the pH of the solution is between about 5.5 and 6.3; and
   c) adding about 3 to 10 ml of the amikacin solution to a container in order to generate a unit dose; wherein the unit dose comprises a preservative-free liquid composition for aerosolization having a pH of about 5.5 to about 6.3 and a shelf life of at least two years at room temperature without the formation of precipitate, wherein the unit dose consists essentially of water and about 400 mg to about 750 mg amikacin, at a concentration of about 125 mg/ml; and wherein the unit dose has an osmolarity ranging from about 90 mOsmol/kg to about 500 mOsmol/kg and a potency of amikacin, from about 500 μg/mg to about 1100 μg/mg.

2. The method of claim 1, wherein the container is in a nebulizer.

3. The method of claim 2, wherein the nebulizer is a vibrating mesh nebulizer.

4. The method of claim 1, wherein about 3 to 6 ml of the amikacin solution is added to the container in step c).

5. The method of claim 1, wherein the container is an ampoule.

6. The method of claim 1 or 5, wherein the container comprises a blow-fill seal.

7. The method of claim 1, wherein the container comprises a vial.

8. The method of claim 1, wherein the container comprises a glass bottle.

9. The method of claim 1, wherein the rubber stopper is a rubber siliconized stopper.

10. A unit dose of an aqueous amikacin composition, wherein the unit dose is prepared according to a method comprising the steps of:
   a) preparing an amikacin solution by dissolving amikacin sulfate in preservative-free water for injection by stirring;
   b) adjusting the pH of the amikacin solution, if necessary, until the pH of the solution is between about 5.5 and 6.3; and
   c) adding about 3 to 10 ml of the amikacin solution to a container in order to generate a unit dose; wherein the unit dose comprises a preservative-free liquid composition for aerosolization having a pH of about 5.5 to about 6.3 and a shelf life of at least two years at room temperature without the formation of precipitate, wherein the unit dose consists essentially of water and about 400 mg to about 750 mg amikacin, at a concentration of about 125 mg/ml; and wherein the unit dose has an osmolarity ranging from about 90 mOsmol/kg to about 500 mOsmol/kg and a potency of amikacin, from about 500 μg/mg to about 1100 μg/mg.

* * * * *